US007344709B2

(12) United States Patent
Parsons et al.

(10) Patent No.: US 7,344,709 B2
(45) Date of Patent: Mar. 18, 2008

(54) TREATMENT OF HEPATITIS C IN THE ASIAN POPULATION WITH SUBCUTANEOUS INTERFERON-BETA

(75) Inventors: Ian Parsons, Coppet (CH); Theodor Wee Tit Gin, Singapore (SG); Birgit Maschek, Windham, NH (US)

(73) Assignee: Laboratories Serono SA, Coinsins, Vaud (CH)

( * ) Notice: Subject to any disclaimer, the term of this patent is extended or adjusted under 35 U.S.C. 154(b) by 261 days.

(21) Appl. No.: 10/515,032

(22) PCT Filed: May 28, 2003

(86) PCT No.: PCT/EP03/50202

§ 371 (c)(1),
(2), (4) Date: Jul. 11, 2005

(87) PCT Pub. No.: WO03/101478

PCT Pub. Date: Dec. 11, 2003

(65) Prior Publication Data

US 2006/0029572 A1    Feb. 9, 2006

(30) Foreign Application Priority Data

Jun. 3, 2002    (EP)    .................. 02100632

(51) Int. Cl.
*A61K 38/19*    (2006.01)
*A61K 38/21*    (2006.01)
*C07K 14/555*    (2006.01)
*C07K 14/565*    (2006.01)

(52) U.S. Cl. .................. 424/85.6; 424/85.1; 424/85.4; 530/350; 530/351

(58) Field of Classification Search ............... None
See application file for complete search history.

(56) References Cited

U.S. PATENT DOCUMENTS

| | | | |
|---|---|---|---|
| 4,588,585 | A | 5/1986 | Mark et al. |
| 4,737,462 | A | 4/1988 | Mark et al. |
| 4,904,584 | A | 2/1990 | Shaw |
| 4,959,314 | A | 9/1990 | Mark et al. |
| 4,965,195 | A | 10/1990 | Namen et al. |
| 5,017,691 | A | 5/1991 | Lee et al. |
| RE33,653 | E | 7/1991 | Mark et al. |
| 5,116,943 | A | 5/1992 | Koths et al. |

FOREIGN PATENT DOCUMENTS

WO    WO 99/55377 A3    11/1999

OTHER PUBLICATIONS

Barbaro et al., "Intravenous Recombinant Interferon-Beta versus Interferon-Alpha-2b and Ribavirin in Combination for Short-Term Treatment of Chronic Hepatitis C Patients Not Responding to Interferon-Alpha," Scandinavian Journal of Gastroenterology, vol. 34 No. 9, pp. 928-933 (Sep. 1999).*

Buchwalder et al., "Pharmacokinetics and pharmacodyamics of IFN-beta1a in healthy volunteers," Jouranl of Interferon and Cytokine Research, vol. 20 No. 10, pp. 857-866 (2000).*

Cheng et al., "Racial differences in responses to interferon-β-1a in chronic hepatitis C unresponsive to interferon-α: A better response in Chinese patients," Journal of Viral hepatits, vol. 11 No. 5, pp. 418-426 (Sep. 2004).*

Kakumu et al., "A pilot study of ribavirin and interferon beta for the treatment of chronic hepatitis C," Gastroenterology, vol. 105 No. 2, pp. 507-512 (1993).*

Alter, M. J. et al. "The Natural History of Community-Acquired Hepatitis C in the United States" *The New England Journal of Medicine*, 1992, pp. 1899-1905, vol. 327, No. 27.

Alter, M. J. et al. "The Prevalence of Hepatitis C Virus Infection in the United States, 1988 through 1994" *The New England Journal of Medicine*, 1999, pp. 556-562, vol. 341.

Bacon, B.R. et al. "Lymphoblastoid Interferon Improves Long-Term Response to a Six Month Course of Treatment when compared with Recombinant Interferon Alfa 2b: Results of an International Trial" *Hepatology*, 1995, p. 152A, vol. 22.

Bedossa, P. et al. "An Algorithm for the Grading of Activity in Chronic Hepatitis C" *Hepatology*, 1996, pp. 289-293, vol. 24, No. 2.

Bonkovsky, H. L. et al. "Iron and Chronic Viral Hepatitis" *Hepatology*, 1997, pp. 759-768, vol. 25.

Brand, C.M. et al. "Antibodies Developing Against a Single Recombinant Interferon Protein may Neutralize many other Interferon-α Subtypes" *Journal of Interferon Research*, 1993, pp. 121-125, vol. 13.

Cavalli-Sforza, L. "Genes, Peoples and Languages" *Scientific American*, Nov. 1991, pp. 72-78.

Conjeevaram, H. S. et al. "Predictors of a Sustained Beneficial Response to Interferon Alfa Therapy in Chronic Hepatitis C" *Hepatology*, 1995, pp. 1326-1329, vol. 22, No. 4.

Cuzick, J. "A Wilcoxon-Type Test for Trend" *Statistics In Medicine*, 1985, pp. 87-90, vol. 4.

Davis, G. L. "Recombinant α-interferon Treatment of Non-A, Non-B (Type C) Hepatitis: Review of Studies and Recommendations for Treatment" *Journal of Hepatology*, 1990, pp. S72-S77, vol. 11.

Derynck, R. et al. "Isolation and Structure of a Human Fibroblast Interferon Gene" *Nature*, 1980, pp. 542-547, vol. 285.

(Continued)

*Primary Examiner*—Zachariah Lucas
(74) *Attorney, Agent, or Firm*—Saliwanchik, Lloyd & Saliwanchik

(57) ABSTRACT

The present invention relates to the use of recombinant IFN-beta for the production of a medicament for the treatment of HCV infection by subcutaneous administration to patients of Asian race, which failed to respond to a previous treatment with interferon-alpha, is herein reported. According to a preferred embodiment of the invention, this treatment can be better and further focused to those patients which after at least 4 weeks of initial treatment with IFN-beta show HCV RNA clearance.

7 Claims, 4 Drawing Sheets

OTHER PUBLICATIONS

Douglas, D. D. et al. "Randomized Controlled Trial of Recombinant Alpha-2a-Interferon for Chronic Hepatitis C. Comparison of Alanine Aminotransferase Normalization versus Loss of HCV RNA and Anti-HCV IgM" *Digestive Diseases and Sciences*, 1993, pp. 601-607, vol. 38, No. 4.

"NIH Recommends 12-month Interferon Therapy for Hepatitis C" *Scrip*, No. 2221, Apr. 8, 1997, pp. 25-26, PJB Publications Ltd.

Habersetzer, F. et al. "A Pilot Study of Recombinant Interferon Beta-1a for the Treatment of Chronic Hepatitis C" *Liver*, 2000, pp. 437-441, vol. 20.

Hoofnagle, J. H. et al. "The Treatment of Chronic Viral Hepatitis" *The New England Journal of Medicine Drug Therapy*, 1997, pp. 347-356, vol. 336, No. 5.

Ishak, K. et al. "Histological Grading and Staging of Chronic Hepatitis" *Journal of Hepatology*, 1995, pp. 696-699, vol. 22.

Kishihara, Y. et al. "A Preliminary Study of Retreatment of Chronic Hepatitis C with Interferon" *Fukuoka Acta Med.*, 1995, pp. 113-120, vol. 86, No. 4.

Lindsay, K. L. et al. "Response to Higher Doses of Interferon Alfa-2b in Patients with Chronic Hepatitis C: A Randomized Multicenter Trial" *Hepatology*, 1996, pp. 1034-1040, vol. 24.

Lok, A. S-F. et al. "Interferon Antibodies may Negate the Antiviral Effects of Recombinant α-Interferon Treatment in Patients with Chronic Hepatitis B Virus Infection" *Hepatology*, 1990, pp. 1266-1270, vol. 12, No. 6.

Mark, D. F. et al. "Site-Specific Mutagenesis of the Human Fibroblast Interferon Gene" *Proc. Natl. Acad. Sci. USA*, Sep. 1984, pp. 5662-5666. vol. 81.

McCaughan, G. W. "Working Party Report: Hepatitis. Asian Perspectives on Viral Hepatitis: Hepatitis C Virus Infection" *Journal of Gastroenterology and Hepatology*, 2000, pp. G90-G93, vol. 15.

McHutchison, J. G. et al. "Interferon Alfa-2b Alone or in Combination with Ribavirin as Initial Treatment for Chronic Hepatitis C" *The New England Journal of Medicine*, 1998, pp. 1485-1492, vol. 339, No. 21.

McIntyre N. et al. "Cirrhosis, Portal Hypertension and Ascites" In Weatherall DJ. et. al., editors. *Oxford Textbook of Medicine*, Chapter 14.29, 1996, pp. 2085-2100, Oxford University Press.

McOmish, F. et al. "Geographical Distribution of Hepatitis C Virus Genotypes in Blood Donors: an International Collaborative Survey" *Journal of Clinical Microbiology*, Apr. 1994, pp. 884-892, vol. 32, No. 4.

Milella, M. et al. "Neutralizing Antibodies to Recombinant Alpha-Interferon and Response to Therapy in Chronic Hepatitis C Virus Infection" *Liver*, 1993, pp. 146-150, vol. 13.

O'Brien, P. C. "Procedures for Comparing Samples with Multiple Endpoints" *Biometrics*, 1984, pp. 1079-1087, vol. 40.

Omata, M. et al. "Resolution of Acute Hepatitis C after Therapy with Natural Beta Interferon" *The Lancet*, 1991, pp. 914-915, vol. 338.

Perez, R. et al. "Clinical Efficacy of Intramuscular Human Interferon-β vs Interferon-α2b for the Treatment of Chronic Hepatitis C" *Journal of Viral Hepatitis*, 1995, pp. 103-106, vol. 2.

Piccinino, F. et al. "Non Responders to Interferon Therapy among Chronic Hepatitis Patients Infected with Hepatitis C Virus" *Arch. Virol. Suppl.*, 1993, pp. 257-263, vol. 8.

Poynard, T. et al. "Randomized Trial of Interferon α2b Plus Ribavirin for 48 Weeks or 24 Weeks versus Interferon α2b Plus Placebo for 48 Weeks for Treatment of Chronic Infection with Hepatitis C Virus" *The Lancet*, 1998, pp. 1426-1432, vol. 352.

Poynard, T. et. al. "Meta-Analysis of Interferon Randomized Trials in the Treatment of Viral Hepatitis C: Effects of Dose and Duration" *Hepatology*, 1996, pp. 778-789, vol. 24.

PRISMS Study Group "PRISMS-4: Long Term Efficacy of Interferon-β-1a in Relapsing MS" *Neurology*, Jun. 2001, pp. 1628-1636, vol. 56.

Saracco, G. et al. "Long-Term Follow-up of Patients with Chronic Hepatitis C Treated with Different Doses of Interferon-$α_{2b}$" *Hepatology*, 1993, pp. 1300-1305, vol. 18, No. 6.

Scheuer, P. J. "Scoring of Liver Biopsies: Are we Doing it Right?" *Journal of Gastroenterology & Hepatology*, 1996, pp. 1141-1143, vol. 8, No. 12.

Schvarcz, R. et al. "A Randomized Controlled Open Study of Interferon Alpha-2b Treatment of Chronic Non-A, Non-B Post-transfusion Hepatitis: No Correlation of Outcome to Presence of Hepatitis C Virus Antibodies" *Scand. J. Infect. Dis.*, 1989, pp. 617-625, vol. 21.

Shepard, H. M. et al. "A Single Amino Acid Change in IFN-$β_1$ Abolishes its Antiviral Activity" *Nature*, Dec. 1981, pp. 563-565, vol. 294.

Tabor, E. et al. "Hepatitis C Virus, A Causative Infectious Agent of Non-A, Non-B Hepatitis: Prevalence and Structure-Summary of a Conference on Hepatitis C Virus as a Cause of Hepatocellular Carcinoma" *Journal of the National Cancer Institute*, Jan. 15, 1992, pp. 86-90, vol. 84, No. 2.

Takeda, T. et al. "Long-term Therapeutic Efficacy of Interferon for Patients with Chronic Hepatitis C" *Gastroenterolgia Japonica*, 1993, pp. 104-108, vol. 28, Supp. 5.

Tundo, L. "Efficacy Evaluation of Alpha vs Beta Interferon IFN in the Treatment of Chronic Viral Hepatitis" *Hepatology*, Oct. 1993, p. 260A.

Wilkinson, T. "Hepatitis C Virus: Prospects for Future Therapies" *Curr. Op. Invst. Drugs*, 2001, pp. 1516-1522, vol. 2, No. 11.

Zein, N. N. et al. "Hepatitis C Virus Genotypes in the United States: Epidemiology, Pathogenicity, and Response to Interferon Therapy" *Annals of Internal Medicine*, Oct. 15, 1996, pp. 634-639, vol. 125, No. 8.

Iwabuchi, S. et al. "Dynamics of Serum HCV RNA Levels during IFN Therapy in Patients with Chronic Hepatitis C for Prediction of Outcome of IFN Therapy and Beneficial Dosing" *Nippon Rinsho*, Jul. 2001, pp. 1363-1368, vol. 59, No. 7, abstract only, Database Medline 'Online! US National Library of Medicine, Accession No. 11494552.

Castro, A. et al. "Tolerance and Efficacy of Subcutaneous Interferon-β Administered for the Treatment of Chronic Hepatitis C." *Journal of Interferon and Cytokine Research*, 1997, pp. 65-67, vol. 17.

Arase, Y. et al. "A trial of New Interferon for the Patients with Chronic Hepatitis C Resistant to Interferon Therapy" *Nippon Rinsho*, Jul. 2001, pp. 1309-1314, vol. 59, No. 7, abstract only, Database Medline 'Online! US National Library of Medicine, Accession No. 11494543.

Liberati, A.M. et al. "Double-Blind Randomized Phase I Study on the Clinical Tolerance and Biological Effects of Natural and Recombinant Interferon-Beta" *J. Interferon Res.*, Oct. 1992, pp. 329-336, vol. 12, No. 5, abstract only, Database Medline 'Online! US National Library of Medicine, Accession No. 1431312.

Rebif (interferon beta-1a)—Package Insert; May 2002, Serono, Inc., Randolph, MA 02368, XP002210592.

Management of Hepatitis C. NIH Consensus Development Conference Statement, Mar. 24-26, 1997, pp. 1-24, vol. 15, No. 3.

Duby, A. et al. "Using Synthetic Oligonucleotides as Probes" *Current Protocols in Molecular Biology*, 1993, pp. 6.4.1-6.4.10, Supplement 2.

Meinkoth, J. et al. "Hybridization of Nucleic Acids Immobilized on Solid Supports" *Analytical Biochemistry*, 1984, pp. 267-284, vol. 138.

\* cited by examiner

Figure 1     Patient Disposition (Total Population)
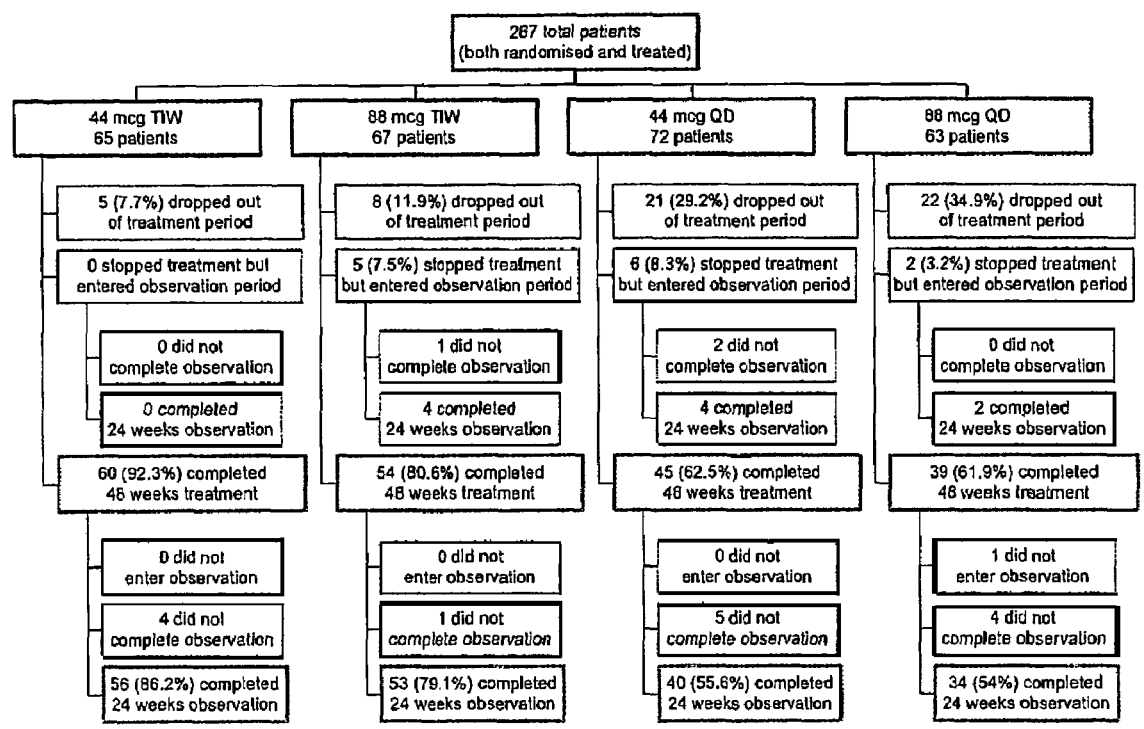

Figure 2    Patient Disposition (Asian Population)
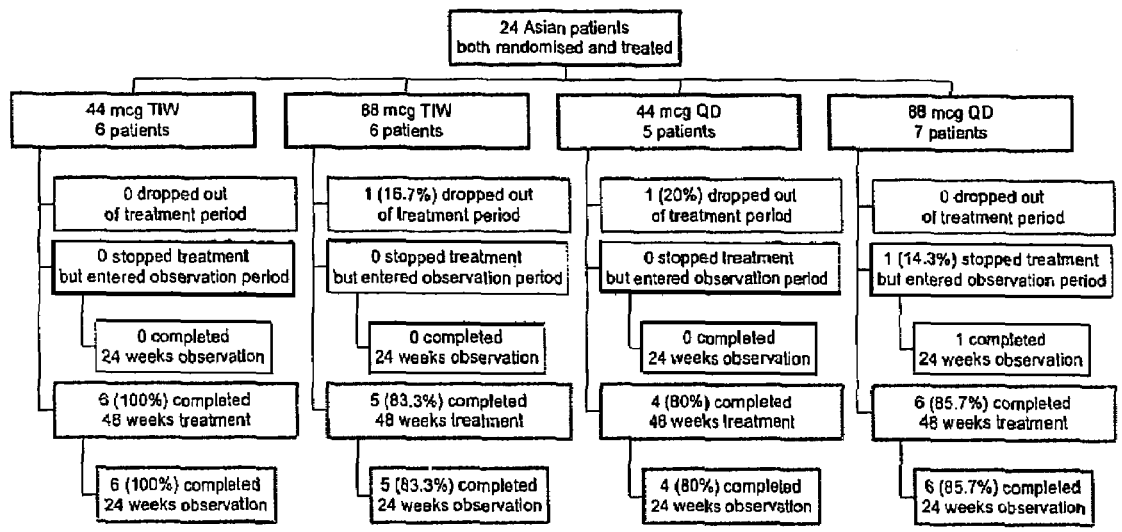
Figure 3    Patient Disposition (Asian vs. Non-Asian Populations)
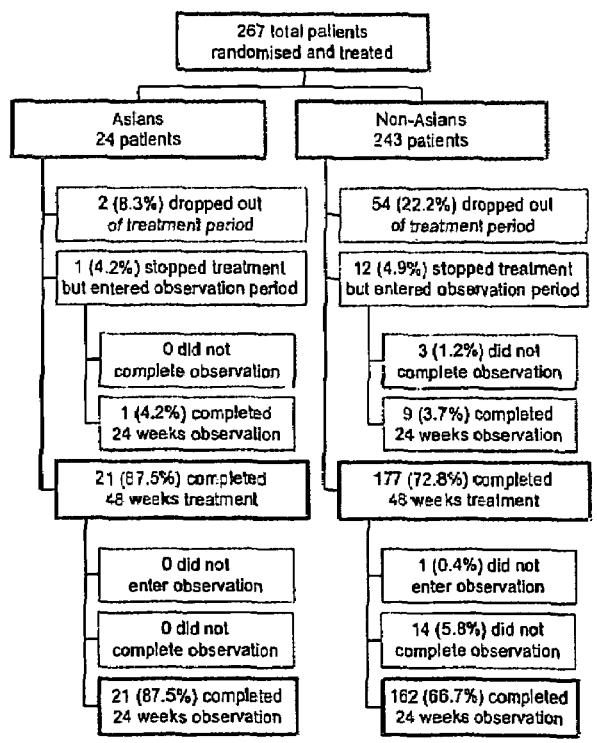

Figure 4  Endpoint Summary: HCV RNA Clearance (Asian vs. Non-Asian Populations)
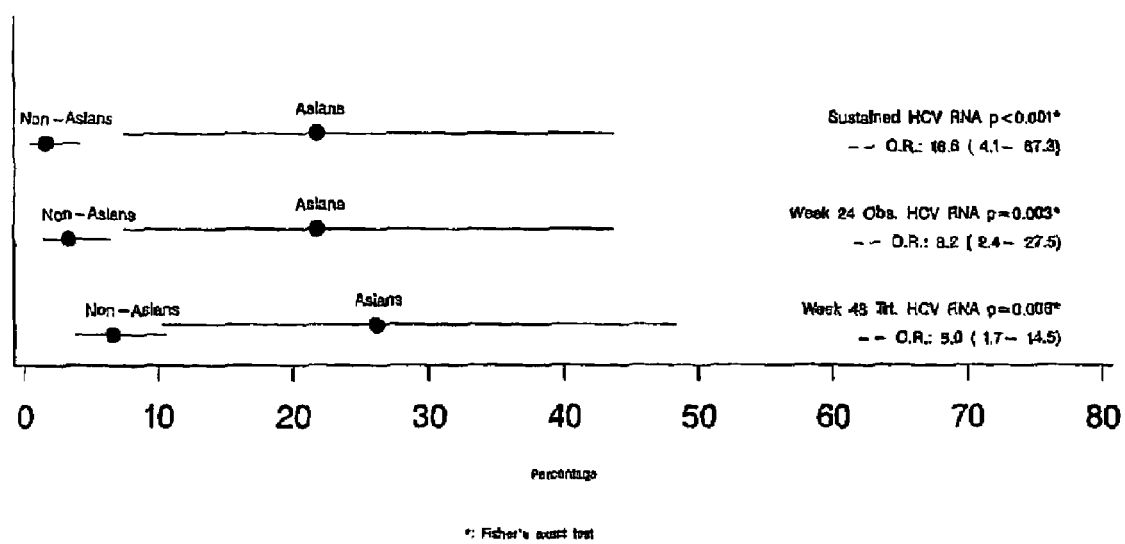

Figure 5    Endpoint Summary: ALT Normalisation (Asian vs. Non-Asian Populations)
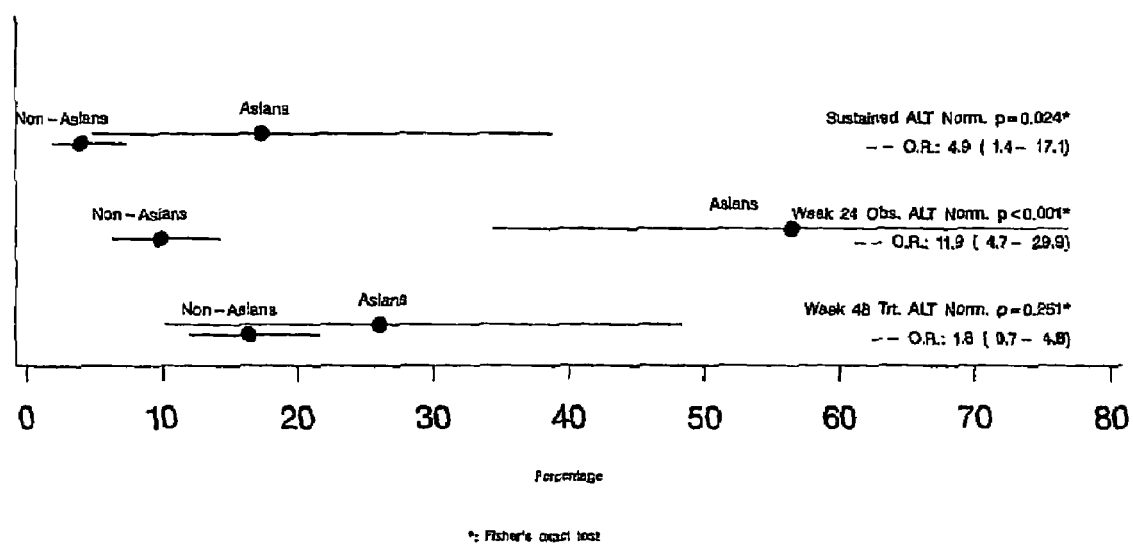

TREATMENT OF HEPATITIS C IN THE ASIAN POPULATION WITH SUBCUTANEOUS INTERFERON-BETA

CROSS-REFERENCE TO RELATED APPLICATION

This application is the U.S. national stage application of International Patent Application No. PCT/EP03/50202, filed May 28, 2003.

FIELD OF THE INVENTION

This invention relates to the use of recombinant IFN-beta for the production of a medicament for the treatment of HCV infection by subcutaneous administration to patients of Asian race, which failed to respond to a previous treatment with interferon alpha.

BACKGROUND OF THE INVENTION

The hepatitis C virus (HCV) produces a state of chronic infection in nearly all acutely infected individuals. Approximately 20% of patients with chronic HCV infection (CHC) develop cirrhosis with subsequent liver failure, portal hypertension, ascites, encephalopathy, and bleeding disorders (Alter M., 1992). Long-term follow-up suggests that these estimates may be conservative (Davis G L, 1990); moreover, chronic HCV infection is strongly associated with hepatocellular carcinoma (Tabor E. et al., 1992).

Interferons (IFNs) are glycoproteins produced by the body in response to a viral infection. They inhibit the multiplication of viruses in protected cells. Consisting of a lower molecular weight protein, IFNs are remarkably non specific in their action, i.e. IFN induced by one virus is effective against a broad range of other viruses. They are however species-specific, i.e. IFN produced by one species will only stimulate antiviral activity in cells of the same or a closely related species. IFNs were the first group of cytokines to be exploited for their potential antitumour and antiviral activities.

The three major IFNs are referred to as IFN-alpha, IFN-beta and IFN-gamma. Such main kinds of IFNs were initially classified according to their cells of origin (leukocyte, fibroblast or T cell). However, it became clear that several types might be produced by one cell. Hence leukocyte IFN is now called IFN-alpha, fibroblast IFN is IFN-beta and T cell IFN is IFN-gamma. There is also a fourth type of IFN, lymphoblastoid IFN, produced in the "Namalwa" cell line (derived from Burkitt's lymphoma), which seems to produce a mixture of both leukocyte and fibroblast IFN.

In particular, human fibroblast interferon (IFN-beta) has antiviral activity and can also stimulate natural killer cells against neoplastic cells. It is a polypeptide of about 20,000 Da induced by viruses and double-stranded RNAs. From the nucleotide sequence of the gene for fibroblast interferon, cloned by recombinant DNA technology, Derynk et al. (Derynk R. et al., Nature 285, 542-547, 1980) deduced the complete amino acid sequence of the protein. It is 166 amino acid long.

Shepard et al. (Shepard H. M. et al., Nature, 294, 563-565, 1981) described a mutation at base 842 (Cys→Tyr at position 141) that abolished its anti-viral activity, and a variant clone with a deletion of nucleotides 1119-1121.

Mark et al. (Mark D. F. et al., Proc. Natl. Acad. Sci. U.S.A., 81 (18) 5662-5666, 1984) inserted an artificial mutation by replacing base 469 (T) with (A) causing an amino acid switch from Cys→Ser at position 17. The resulting IFN-beta was reported to be as active as the 'native' IFN-β and stable during long-term storage (−70° C.).

Rebif® (recombinant human Interferon-beta-1a) is the latest development in interferon therapy for multiple sclerosis (MS) and represents a significant advance in treatment. Rebif® is Interferon (IFN)-beta-1a, produced from mammalian cell lines.

The mechanisms by which IFNs exert their effects are not completely understood. However, in most cases they act by affecting the induction or transcription of certain genes, thus affecting the immune system. In vitro studies have shown that IFNs are capable of inducing or suppressing about 20 gene products.

There is no completely effective therapy for CHC. The best results have been obtained with interferon-alpha, although this is not a universally-recommended therapy. Many clinicians only observe patients with CHC because of the uncertain natural history of HCV infection and the toxicity associated with interferon-alpha.

Most patients with CHC do not achieve complete responses to treatment with interferon-alpha. Controlled trials of interferon-alpha administered for six months resulted in normalisation of serum ALT in 40 to 50% of patients at the end of treatment, but this response was sustained in only 15 to 25% (Hoofnagle J H et al., 1997).

Dose escalations and increased duration of therapy have resulted in small increases in sustained response, but at the cost of increased expense and toxicity (Poynard T. et al., 1996). In addition, the benefit of higher doses is often transient and relapses are common after therapy has been discontinued (Lindsay K L et al., 1996).

A study of 35 non-responders to interferon-alpha reported no benefit from prolongation of therapy from six to 12 months, increasing the dose of interferon-alpha, switching therapy from recombinant to lymphoblastoid interferon or using steroids (Piccinino F et al., 1993).

The natural history of HCV infection following lack of response to interferon-alpha has not been adequately studied, but in one study follow-up of 28 patients for at least 2 years after therapy found only one case of eventual remission at 16 months (normalisation of ALT and disappearance of HCV RNA) (Takeda T et al., 1993).

Several factors have been found to be associated with greater probability of long-term sustained response to interferon-alpha: non-type 1 genotype, low serum HCV RNA concentration, shorter duration of infection, lower body weight, mild activity on liver biopsy, absence of cirrhosis and low levels of serum ferritin, iron, transferrin saturation and hepatic iron concentration (Schvarcz R et al., 1989, Bacon B R et al., 1995, Conjeevaram H S et al., 1995, Bonkovsky H L et al., 1997).

Patients with CHC who fail to achieve a sustained response after interferon-alpha therapy are thought to have a more aggressive disease course, possibly due to the selection of resistant genotypes, but the development of neutralising antibodies to interferon-alpha may also be a contributing factor. There appears to be a strong correlation between development of neutralising antibodies to interferon-alpha-2a and lack of clinical benefit, in both CHC and hepatitis B virus (HBV) infections (Douglas D D et al., 1993, Milella M M et al., 1993, Lok A S F et al., 1990). In fact, the development of antibodies to a single recombinant type of interferon-alpha may neutralise other Interferon-alpha subtypes (Brand C M et al., 1993).

There is relatively little experience with interferon-beta in HCV infection. Very promising results have been reported for interferon-beta therapy of acute HCV infection, with 7 of 11 patients achieving sustained normalisation of ALT at one year compared to only one of 14 controls (Omata M et al., 1991). The eleven patients were treated for an average of 30 days with a mean IV dose of 52 MU of fibroblast-derived, "native", and interferon-beta. Notably, no significant toxicity was reported.

Today, in Japan natural IFN-beta is commonly used for the treatment of chronic hepatitis C and the recommended regimen is a daily dose of 3-6 MIU administered i.v. for 6-8 weeks (see Habersetzer et al., Liver, 2000, 20, 438, 4th line).

Very poor clinical efficacy of intramuscular administration of IFN-beta (3 MU t.i.w) in HCV patients of non-Asian race has been shown (Perez R. et al., J. Virol. Hepat. 1995, 2(2), 103-6).

Always in non-Asian (Caucasian) HCV patients subcutaneous administration (9 or 12 MU) of recombinant IFN-beta has shown efficacy at least in a group of patients (Habersetzer et al., Liver, 2000, 20 437-441).

Kishiara et al. (Fukukoka Acta Med., 86(4), 113-20, 1995) disclose a treatment with natural IFN-beta administered i.v. at a dose of 6MIU to HCV patients not responding to IFN-alpha.

In a preliminary comparative study of interferon-alpha vs. interferon-beta in HBV and HCV, response rates were 81% for interferon-alpha and 86% for interferon-beta, with similar response rate maintenance at 6 months (72% for interferon-alpha and 79% for interferon-beta) (Tundo L, 1993). Notably, side effects led to interruption of therapy for 24% of the interferon-alpha group compared to 0% of the interferon-beta group.

The encouraging initial results of some previous studies carried out by the Applicant, along with the good safety and tolerability profile of IFN-beta-1a, led to the design of the study, which explored higher and more intense dose regimens for a longer treatment period in patients with chronic hepatitis C who had failed treatment with IFN-alpha.

DESCRIPTION OF THE INVENTION

Because of a spontaneous report of good efficacy results by the Investigator in the Taiwanese centre, exploratory analyses by centre and by demographic characteristics were performed, which led to identification of differences between patients of Asian and non-Asian origin. The study's analysis plan was therefore amended to include complete evaluation of these two populations.

The main object of the present invention is the use of recombinant IFN-beta for the production of a medicament for the treatment of HCV infection by subcutaneous administration to patients of Asian race, which failed to respond to a previous treatment with interferon alpha.

Another object of the present invention is, therefore, the method for treating HCV infection comprising administering subcutaneously an effective amount of IFN-beta, together with a pharmaceutically acceptable excipient, to patients of Asian race, who failed to respond to a previous treatment with IFN-alpha.

An "effective amount" refers to an amount of the active ingredients that is sufficient to affect the course and the severity of the disease, leading to the reduction or remission of such pathology. The effective amount will depend on the route of administration and the condition of the patient.

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

Besides the pharmaceutically acceptable carrier, the compositions of the invention can also comprise minor amounts of additives, such as stabilizers, excipients, buffers and preservatives.

The term "recombinant interferon-beta (IFN-beta)", as used in the present invention, is intended to include human fibroblast interferon, as obtained by DNA recombinant techniques from prokaryotic or eukaryotic host cells as well as its salts, functional derivatives, variants, analogs and fragments.

"Functional derivatives" as used herein covers derivatives which may be prepared from the functional groups which occur as side chains on the residues or the N- or C-terminal groups, by means known in the art, and are included in the invention as long as they remain pharmaceutically acceptable, i.e., they do not destroy the biological activity of the proteins as described above, i.e., the ability to bind the corresponding receptor and initiate receptor signaling, and do not confer toxic properties on compositions containing it. Derivatives may have chemical moieties, such as carbohydrate or phosphate residues, provided such a derivative retains the biological activity of the protein and remains pharmaceutically acceptable.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (e.g., that of seryl or threonyl residues) formed with acyl moieties. Such derivatives may also include for example, polyethylene glycol side-chains, which may mask antigenic sites and extend the residence of the molecule in body fluids.

Of particular importance is a protein that has been derivatized or combined with a complexing agent to be long lasting. For example, pegylated versions, or proteins genetically engineered to exhibit long lasting activity in the body, can be used according to the present invention. A pegylated version of interferon-beta-1a has been described in WO 99/55377 and is considered as included in the definition of interferon-beta according to the present application.

The term "derivatives" is intended to include only those derivatives that do not change one amino add to another of the twenty commonly occurring natural amino acids.

The term "salts" herein refers to both salts of carboxyl groups and to acid addition salts of amino groups of the proteins described above or analogs thereof. Salts of a carboxyl group may be formed by means known in the art and include Inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the protein relevant to the present invention, i.e., the ability to bind to the corresponding receptor and initiate receptor signaling.

A "fragment" according to the present invention refers to any subset of the molecules, that is, a shorter peptide, which retains the desired biological activity. Fragments may readily be prepared by removing amino acids from either end of the molecule and testing the resultant for its properties as a receptor agonist. Proteases for removing one amino acid at a time from either the N-terminal or the C-terminal of a polypeptide are known, and so determining fragments, which retain the desired biological activity, involves only routine experimentation.

A "variant" according to the present invention refers to a molecule, which is substantially similar to either the entire proteins defined above or a fragment thereof. Variant peptides may be conveniently prepared by direct chemical synthesis of the variant peptide, using methods well known in the art. Of course, such variant would have similar receptor binding and signal initiating activity as the corresponding naturally occurring protein.

Amino acid sequence variants of the protein defined above can be prepared by mutations in the DNAs, which encode the synthesized derivatives. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure.

At the genetic level, these variants ordinarily are prepared by site-directed mutagenesis of nucleotides in the DNA encoding the peptide molecule, thereby producing DNA encoding the variant, and thereafter expressing the DNA in recombinant cell culture. The variants typically exhibit the same qualitative biological activity as the non-variant peptide.

An "analog" of the protein defined above, according to the present invention, refers to a non-natural molecule, which is substantially similar to either, the entire molecules or to an active fragment thereof. Such analog would exhibit the same activity as the corresponding naturally occurring protein.

The types of substitutions, which may be made to interferon-beta, according to the present invention, may be based on analysis of the frequencies of amino acid changes between homologous proteins of different species. Based upon such analysis, conservative substitutions may be defined herein as exchanges within one of the following five groups:

Small, aliphatic, non-polar or slightly polar residues:
 Ala, Ser, Thr, Pro, Gly II. Polar, negatively charged residues and their amides:
 Asp, Asn, Glu, Gln
 III. Polar, positively charged residues:
 His, Arg, Lys
 IV. Large, aliphatic non-polar residues:
 Met, Leu, Ile, Val, Cys
 V. Large aromatic residues:
 Phe, Tyr, Trp
 Within the foregoing groups, the following substitutions are considered to be "highly conservative":
 Asp/Glu
 His/Arg/Lys
 Phe/Tyr/Trp
 Met/Leu/Ile/Val Semi-conservative substitutions are defined to be exchanges between two of groups (I)-(IV) above which are limited to supergroup (A), comprising (I), (II), and (III) above, or to supergroup (B), comprising (IV) and (V) above. Substitutions are not limited to the genetically encoded or even the naturally-occurring amino acids. When the epitope is prepared by peptide synthesis, the desired amino acid may be used directly. Alternatively, a genetically encoded amino acid may be modified by reacting it with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxylmethyl or carboxyamidomethyl derivatives. Cysteinyl residues also are derivatized by reaction with bromotrifluoroacetone, alpha-bromo-beta-(5-imidazoyl)propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Parabromophenacyl bromide is also useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino acid-containing residues include imidoesters such as methyl picolinimidate; pyridoxal phosphate; pyridoxal; chloroborohydride; trinitrobenzenesulfonic acid; O-methyliosurea; 2,4-pentanedione; and transaminase-catalyzed reaction with glyoxylate.

Arginyl residues are modified by reaction with one or several conventional reagents, among them phenylglyoxal; 2,3-butanedione; and ninhydrin. Derivatization of arginine residues requires that the reaction be performed in alkaline conditions because of the high pKa of the guanidine functional group. Furthermore, these reagents may react with the groups of lysine, as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and ε-nitro derivatives, respectively.

Carboxyl side groups (aspartyl or glutamyl) are selectively modified by reaction with carbodiimides (R'N—C—N—R') such as 1-cyclohexyl-3-[2-morpholinyl-(4-ethyl)] carbodiimide or 1-ethyl-3-4-azonia-4,4-dimethylpentyl) carbodimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Examples of production of amino acid substitutions in proteins which can be used for obtaining analogs for use in the present invention include any known method steps, such as presented in U.S. Pat. Nos. RE 33,653; 4,959,314; 4,588, 585 and 4,737,462, to Mark et al; U.S. Pat. No. 5,116,943 to Koths et al; U.S. Pat. No. 4,965,195 to Namen et al; and U.S. Pat. No. 5,017,691 to Lee, et al, and lysine substituted proteins presented in U.S. Pat. No. 4,904,584 (Shaw et al).

Preferably, the variant or analog, as defined above, will have a core sequence, which is the same as that of the "native" sequence or biologically active fragment thereof, which has an amino add sequence having at least 70% identity to the native amino add sequence and retains the biological activity thereof. More preferably, such a sequence has at least 80% identity, at least 90% identity, or most preferably at least 95% identity to the native sequence.

The term "sequence identity" as used herein means that the sequences are compared as follows. The sequences are aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

Analogs or variants in accordance with the present invention may also be determined in accordance with the following procedure. The DNA of the native sequence is known to the prior art and is found in the literature. Polypeptides encoded by any nucleic acid, such as DNA or RNA, which hybridizes to the complement of the native DNA or RNA under highly stringent or moderately stringent conditions, as long as that polypeptide maintains the biological activity of the native sequence, are also considered to be within the scope of the present invention.

Stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature Tm of the DNA—DNA hybrid: Tm=81.5° C.+16.6 ($_{Log}$M)+0.41 (% GC)−0.61 (% form)−500/L, where M is the molarity of monovalent cations, % GC is the percentage of G and C nucleotides in the DNA, % form is the percentage of formami de in the hybridization solution, and L is the length of the hybrid in base pairs. For each 1° C. that the Tm is reduced from that calculated for a 100% identity hybrid, the amount of mismatch permitted is increased by about 1%. Thus, if the Tm used for any given hybridization experiment at the specified salt and formamide concentrations is 10° C. below the Tm calculated for a 100% hybrid according to equation of Meinkoth, hybridization will occur even if there is up to about 10% mismatch.

As used herein, highly stringent conditions are those, which are tolerant of up to about 15% sequence divergence, while moderately stringent conditions are those, which are tolerant of up to about 20% sequence divergence. Without limitation, examples of highly stringent (12-15° C. below the calculated Tm of the hybrid) and moderately (15-20° C. below the calculated Tm of the hybrid) conditions use a wash solution of 2×SSC (standard saline citrate) and 0.5% SDS at the appropriate temperature below the calculated Tm of the hybrid. The ultimate stringency of the conditions is primarily due to the washing conditions, particularly if the hybridization conditions used are those, which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5× Denhardt's reagent, 0.5% SDS, 100 µg/ml denatured, fragmented salmon sperm DNA at a temperature approximately 20° to 25° C. below the Tm. If mixed probes are used, it is preferable to use tetramethyl ammonium chloride (TMAC) instead of SSC (Ausubel, 1987-1998).

While the present invention provides recombinant methods for making the above-defined derivatives, these derivatives may also be made by conventional protein synthesis methods, which are well known to those skilled in the art.

According to the present invention "a race" is a population that can be distinguished as a distinct subgroup within a species (e.g. the human species). A race possesses a unique and distinct ensemble of genes, and is identified by the traits (both mental and physical) produced by the genetic ensemble. Members of the same race share distinguishing genetic characteristics, because they share a common genetic ancestry and a consequently similar genetic ensemble.

Based on the nuclear DNA studies of Luigi Cavalli Sforza and his colleagues at least 6 human races/populations can be defined: the Caucasoid (which include the European and Indian populations), the African, the Asian, the Arctic, the American Indian, and the Pacific one (L. Cavalli-Sforza, Scientific American, 72-78, November 1991).

According to the present invention "Asian" means any person having origins in any of the original peoples of China, Mongolia, Taiwan, Singapore, Korea, Japan, Vietnam, Cambodia, Laos, Burma, Thailand, Malaysia, Indonesia and Philippines.

"Non-Asian" is herein intended to refer to all the other human races/populations, which do not fall under the above-definition of "Asian".

Patients normally are requested to self-identify by "race" or the doctor on the basis of their somatic traits and/or the country of origin assigns the race.

According to the present invention, "patients who failed to respond to a previous treatment with IFN-alpha" are those HCV patents who underwent a previous treatment with any type (or types) of interferon-alpha (at least 12 weeks of treatment at a dose of at least 3 MIU 3 times a week), with one of the following outcomes: (a) failure to normalise serum ALT, or (b) normalisation of ALT followed by breakthrough (ALT elevation) before the end of therapy. The dosages and the regimens can be selected by the doctor depending on the severity if the disease, the age and the sex of the patient. According to the present applications the following four regimens and dosages have been used.

Regimen A: 12 MIU (44 mcg) recombinant IFN-beta-1a three times a week,

Regimen B: 12 MIU (44 mcg) recombinant IFN-beta-1a daily,

Regimen C: 24 MIU (88 mcg) recombinant IFN-beta-1a three times a week, or

Regimen D: 24 MIU (88 mcg) recombinant IFN-beta-1a daily.

According to a preferred embodiment of the invention, the treatment with IFN-beta is to be carried out only on the subgroup of patients who show HCV RNA clearance after 4 weeks of treatment In fact it has been noted that for this subgroup of patients the probability that the treatment will be successful after the 48 weeks of treatment is very high, close to 100%. "HCV RNA clearance" means absence of detectable HCV RNA in the serum of the treated patients.

In other words the treatment of the present invention may be advantageously preceded by a "test-phase", in which the patients undergo the same treatment with IFN-beta for 4 weeks and at the end of this "test-phase" preferentially the patients who show HCV RNA clearance are encouraged to carry out the treatment for more weeks.

According to a further preferred embodiment of the present invention the treatment with IFN-beta can be coupled with a concomitant treatment with another antiviral drug. The most commonly used antiviral drug in the treatment of HCV is ribavirin (a nucleoside analog), but other drugs show some potential in this treatment and are listed in a recent review (T Wilkinson, Curr. Op. Invst. Drug, 2(11), 1516-22, 2002) and include serine protease inhibitors, inhibitors of the RNA-dependent RNA polymerase (RdRp) and helicase inhibitors. These drugs can be administered simultaneously, separately or sequentially when combined with recombinant IFN-beta.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention. The Examples will refer to the following Figures.

LIST OF ABBREVIATIONS

A Asian
AE Adverse event
ALT Alanine aminotransferase (SGPT)
ANA Anti-nuclear antibodies
AST Aspartate aminotransferase (SGOT)
BUN Blood urea nitrogen
C Cirrhotic
CHC Chronic hepatitis C
CI Confidence interval
CR Complete Response
CRF Case Report Form
CT Computed tomography
ELISA Enzyme-linked immunoabsorbent assay
H & E Haematoxylin & eosin
HAI Histological Activity Index
HBc Hepatitis B core antigen
HBe Hepatitis B e antigen
HBsAg Hepatitis B surface antigen
HBV Hepatitis B virus
hCG Human chorionic gonadotropin
HCV Hepatitis C virus
HIV Human immunodeficiency virus
IEC Independent ethics committee
IFN Interferon
IgM Immunoglobulin M
IM Intramuscular(ly)
INR International Normalised Ratio
IRB Institutional Review Board
IU International unit(s)
IV Intravenous(ly)
l Litre(s)
LU Laboratory units
mcg Microgram(s)
mcmol Micromole(s)
mEq Milliequivalent(s)
MIU Million international units ($10^6$ IU)
ml Milliliter(s)
mmHg Millimeter(s) of mercury
mmol Millimole(s)
MRI Magnetic resonance imaging (scan)
MU Million units ($10^6$ U)
NA Non-Asian
NAb Neutralising antibody (antibodies)
NANBH Non-A, non-B hepatitis
NC Non-cirrhotic
NU Neutralising units
OD Optical density
OR Odds ratio
PCR Polymerase chain reaction
pmol Picomole(s)
PO Peros—By mouth
PT Prothrombin time
QD Every day
RT-PCR Reverse transcription polymerase chain reaction
SC Subcutaneous(ly)
std Standard deviation
SGOT Serum glutamic oxaloacetic transaminase (AST)
SGPT Serum glutamic pyruvic transaminase (ALT)
SMA Smooth muscle antibodies
TIBC Total iron binding capacity
TIW Three times a week
VSV Vesicular stomatitis virus
WBC White blood cell(s)
WHO World Health Organization
WISH A human amniotic cell line

DESCRIPTION OF THE FIGURES

FIG. 1 presents patient disposition over the course of the study for the total population: 198 of the 267 randomised patients completed 48 weeks of treatment (74.2%), and 183 completed both the treatment and the observation periods (68.5%). Fifty-six (56) patients dropped out before completing the treatment period.

FIG. 2 also reports patient disposition over the course of the study, but limited to the Asian population: Twenty-one (21) of the 24 Asian patients completed 48 weeks of treatment (87.5%), and all of these patients went on to complete the observation period.

FIG. 3 also deals with patient disposition over the course of the time, but it presents a comparison between Asian and non-Asian population. From the Figure it can be noted that the completion rate among Asian patients was noticeably higher than that among non-Asians: 87.5% completed the treatment period compared to 72.8% (177 of 243) for non-Asians, and 87.5% completed both treatment and follow-up compared to 66.7% (162 of 243) for non-Asians.

FIG. 4 reports a comparison of main efficacy results between Asian and non-Asian patients for the endpoint associated with HCV RNA clearance. The dots represent the percentage of patients in each population who achieved the endpoint and the horizontal lines represent confidence intervals for these percentages; unadjusted odds ratios (OR) and confidence intervals (CI) for these odds ratios are also presented. Although the number of Asian patients was relatively small, Asians were significantly more likely than non-Asians to achieve complete HCV RNA clearance at Week 48 of treatment (unadjusted OR 5.0; CI for odds ratio [1.7-14.51]; p=0.006), at Week 24 of observation (unadjusted OR 8.2; CI for odds ratio [2.4-27.5]; p=0.003) and at both time points (sustained virological response, the primary efficacy endpoint of the study: unadjusted OR 16.6; CI for odds ratio [4.1-67.3]; p<0.001).

FIG. 5 reports a comparison of main efficacy results between Asian and non-Asian patients for the endpoint associated with ALT normalization. The dots represent the percentage of patients in each population who achieved the endpoint and the horizontal lines represent confidence intervals for these percentages; unadjusted odds ratios (OR) and confidence intervals (CI) for these odds ratios are also presented. Asians were also more likely than non-Asians to have normal serum ALT: the difference was not statistically significant at Week 48 of treatment (unadjusted OR 1.8; CI for odds ratio [0.7-4.8]; p=0.251), but at Week 24 of observation the unadjusted odds ratio for Asians vs. non-Asians was 11.9 (CI for odds ratio [4.7-29.9]; p<0.001), and the unadjusted odds ratio for Asians vs. non-Asians for sustained ALT normalisation was 4.9 (CI for odds ratio [1.4-17.1]; p=0.024).

EXAMPLES

Selection of Study Population

It was planned to enrol approximately 250 patients, 200 without cirrhosis and 50 with compensated cirrhosis as defined in the following section. To be eligible for inclusion, patients had to satisfy all of the following criteria within 28 days prior to Study Day 1, which was defined as the first day of treatment with IFN beta-1a: any exceptions had to be approved by the Investigator at the time of enrolment.

Inclusion Criteria

1. Hepatitis C infection, established by serum positivity for HCV RNA (by RT-PCR).
2. Previous treatment with any type (or types) of interferon-alpha (at least 12 weeks of treatment at a dose of at least 3 MIU 3 times a week), with one of the following outcomes:
   i. Failure to normalise serum ALT, or
   ii. Normalisation of ALT followed by breakthrough (ALT elevation) before the end of therapy.
3. Patients who achieved normalisation of serum ALT during treatment with IFN-alpha but relapsed after treatment discontinuation were not eligible.
4. Histological features of chronic hepatitis, without evidence of other liver disease, in a liver biopsy taken within the 3 months prior to Study Day 1 and after the end of treatment with interferon-alpha. Liver biopsies had to be available for central review.
5. For four or more patients per centre (to a total of approximately 50): compensated cirrhosis, defined by the following histological and clinical criteria:
   i. A diagnosis of probable or definite cirrhosis on liver biopsy, using either the modified Knodell Histological Activity Index (Ishak K et al., 1995) or the Metavir Algorithm (Bedossa P et al., 1998), and
   ii. A maximum Child-Pugh score (McIntyre N et al., 1996) of 6, with no evidence of hepatic encephalopathy or ascites.
6. Discontinuation of interferon-alpha therapy at least 3 months before Study Day 1.
7. Abnormal serum ALT concentrations measured on two occasions at least 4 weeks apart during any three-month interval since discontinuation of interferon-alpha therapy (this could include measurements taken during screening for this study). ALT had to remain abnormal until the beginning of study treatment.
8. Pre-treatment laboratory values within the following ranges:
   a. WBC $\geq 3.0 \times 10^9/l$
   b. Neutrophils $\geq 1.5 \times 10^9/l$
   c. Platelets $\geq 120 \times 10^9/l$
   d. Haemoglobin $\geq 6.8$ mmol/l ($\geq 11$ g/dl)
   e. Serum albumin $\geq 35$ g/l
   f. Total bilirubin $\leq 27.4$ mcmol/l (1.6 mg/dl, unless the patient was known to have Gilbert's syndrome)
   g. Prothrombin time $\leq 2$ sec above control (or INR <1.4)
   h. Serum creatinine $\leq$ upper limit of normal.
9. Age between 18 and 65 years, of either sex.
10. Female patients could not be pregnant or breast-feeding, and had to either be post-menopausal or surgically sterile or use a hormonal contraceptive, intra-uterine device, diaphragm with spermicide, or condom with spermicide for the duration of the study.
11. Confirmation that patients were not pregnant had to be established by a negative serum hCG pregnancy test performed during the 28 days before Study Day 1. This was not required for patients who were post-menopausal or surgically sterile.
12. Written informed consent given before any study-specific procedures, and ability to comply with the protocol for the duration of the study.

Exclusion Criteria

Patients were excluded if any of the following criteria were fulfilled:

Previous treatment with interferon-beta or any systemic antiviral other than interferon-alpha for CHC.

No previous treatment for CHC, or re-treatment with any kind of interferon-alpha after a complete response.

Serologic evidence of acute or chronic hepatitis B infection (positivity for HBsAg or IgM anti-HBc). Patients with a past history of hepatitis B infection were eligible only if their serological profiles indicated cure of HBV (anti-HBsAg and anti-HBe positivity).

Positive HIV serology (active testing was preferred, but was not required if it was opposed by the IEC or IRB).

History, biochemical or morphological evidence of other chronic liver disease including Wilson's disease, alpha$_1$-antitrypsin deficiency (any non-Z phenotype was allowed) or haemochromatosis.

Serological or morphological evidence of autoimmune hepatitis, primary biliary cirrhosis, primary sclerosing cholangitis or other autoimmune disease.

History of acute or chronic liver disease secondary to hepatotoxic drugs.

Alcoholic liver disease (based on assessment of the pre-study liver biopsy).

Suspicion or evidence of liver cancer.

History or current evidence of hepatic failure, variceal bleeding, ascites. hepatic encephalopathy or hepatorenal syndrome.

History of malignancy, with the exceptions of in-situ carcinoma of the cervix or adequately treated basal cell carcinoma of the skin.

Other serious concomitant systemic disorders incompatible with the study (left to the Investigator's discretion).

Current abuse of intravenous drugs or alcohol. Alcohol consumption during the study was not to exceed 10 g per day.

Removal of Patients from Therapy or Assessment

Patients were informed that they had the right to withdraw from the study at any time without prejudice to their medical care, and that they were not obliged to state their reasons. Patients could be withdrawn at any time if the Investigator considered this to be in their best interest.

Patients were required to be withdrawn in the event of life-threatening grade 4 toxicity considered related to interferon beta-1a, or in the event of pregnancy. Patients could also be withdrawn in case of protocol violations, serious intercurrent illnesses or serious adverse events, or for administrative reasons.

If a patient withdrew or was withdrawn prematurely from the study, the primary reason for withdrawal was recorded in the patient's Case Report Form (CRF) and a follow-up evaluation was conducted. Patients who withdrew or were withdrawn for any reason were not replaced.

TREATMENTS

Treatments Administered

Patients received one of the following four treatment regimens:
Regimen A: 12 MIU (44 mcg) IFN-beta-1a three times a week,
Regimen B: 12 MIU (44 mcg) IFN-beta-1a daily,
Regimen C: 24 MIU (88 mcg) IFN-beta-1a three times a week, or
Regimen D: 24 MIU (88 mcg) IFN-beta-1a daily.

Treatment was administered subcutaneously over a period of 48 weeks. Patients were to self-administer the medication, recording details of administration in patient diaries. Injection sites were to be rotated frequently. The IFN-beta-1a used in the treatment was Rebif® (Serono).

Identity of the Investigational Products

IFN-beta-1a was supplied as a sterile, lyophilised powder in glass vials each containing 12 MIU (44 mcg) of IFN-beta-1a plus excipients and stabilisers (human serum albumin, mannitol and sodium acetate). Each vial of study drug included 0.9% sodium chloride solution for use as diluent; Instructions for reconstitution were provided in a patient information booklet and in the study protocol. Lyophilised study drug was to be stored in a secure location at a temperature between 2° and 8° C., and was not to be frozen. The formulation contained no antimicrobial preservative, and therefore reconstituted medication was to be administered immediately. Labelling and packaging were prepared to meet local regulatory requirements.

No blinding was used in this study.

Selection of Doses for the Study

The doses used in this study were chosen based on results of previous studies with natural and recombinant IFN-beta.

Patients self-administered the study drug and recorded details of each administration in diaries that were returned to study personnel along with used and unused study drug vials. Patients were asked to return unused medication to the centre, preferably in its original packaging.

Patients were required to have had prior therapy with IFN-alpha for their chronic hepatitis C. The protocol excluded patients who had received previous treatment with interferon-beta or with antiviral agents other than interferon-alpha for CHC, or who had been retreated with interferon-alpha after a complete response. Patients who abused intravenous drugs or alcohol were also excluded.

During the study, patients could take paracetamol (acetaminophen) if needed to alleviate constitutional symptoms such as fever, myalgias or flu-like symptoms: the total dose was not to exceed 3000 mg per day. Paracetamol could also be given prophylactically at the investigator's discretion. It was suggested that patients be informed that tachyphylaxis to interferon side effects could develop with continued administration, and that administering study medication at bedtime could lessen their perception of such side effects.

Patients were not allowed to receive other immunotherapy, chemotherapy, radiotherapy or corticosteroids during the study, with the exceptions of topical or inhaled corticosteroids and hormonal contraceptives.

Any concomitant therapy that was considered necessary for a patient's welfare and that would not Interfere with the study could be given at the investigator's discretion. Administration of all concomitant therapy was to be recorded in the patient's CRF.

HCV RNA Analysis

HCV RNA analyses were conducted centrally by a laboratory experienced in the detection, quantification and genotyping of HCV, and which was previously involved in the validation steps of the currently used diagnostic tests.

Samples were collected and prepared in accordance with guidelines provided in the study protocol. Qualitative detection of HCV RNA was performed using the Roche COBAS Amplicor HCV Test (version 2.0). Quantification of HCV RNA was performed using a branched DNA assay (Quantiplex HCV RNA 2.0-Chiron/Bayer). Quantification was performed in suitable batches of patient series to minimize inter-assay variation.

Genotyping was performed on pre-treatment serum samples collected during the screening period. The HCV genotype was determined by using the Innolipa line probe assay (Innogenetics) after RT-nested PCR amplification of the 5'-noncoding region of the HCV genomic sequence.

Liver Histology

Among the three classical endpoints employed in studies of antiviral therapy for CHC, namely ALT, HCV RNA and liver histology, the histological evaluation of liver biopsy specimens represents the surrogate end-point considered to be nearest to the 'true' end-points of liver-related morbidity and mortality. Yet, it is also the end-point with the most challenging limitations and sources of bias. Criteria to evaluate histological improvement have not yet been standardized and current practices may differ between regions. These limitations were addressed in this study as follows:

- A pre-treatment liver biopsy demonstrating features of chronic hepatitis, without evidence of other liver disease, was required of all patients for study eligibility. The pre-treatment liver biopsy had to be taken after the end of the previous treatment with interferon-alpha and within the 12 months before Study Day 1 (the first protocol amendment shortened the window to 3 months before Study Day 1). A post-treatment biopsy was to be obtained within a week following the end of the 48 weeks of treatment. All liver biopsies had to be available for central review.
- Samples were to be obtained using normal institutional procedures, and had to contain at least five portal tracts to be evaluable. Three slides were to be prepared from each biopsy sample: one unstained, one stained with haematoxylin & eosin (H & E) and one stained with trichrome (if trichrome was not available, at least one unstained slide and one stained with H & E were to be submitted).
- Biopsy specimens were read centrally by a single pathologist with extensive experience in liver histology. The pathologist was blinded to patient identity, treatment assignment and study centre. Biopsy specimens were read as a biological pair, the pre- and post-treatment slides for one patient being read contemporaneously without knowledge of the order in which the samples were obtained.

Histological assessment used the semi-quantitative Knodell Histological Activity Index (HAI) in a modified version according to Ishak et al. along with a staging system to assess architectural changes, i.e., fibrosis and cirrhosis.

TABLE 1

MODIFIED HISTOLOGICAL ACTIVITY INDEX (HAI)

Modified HAI grading (Necroinflammatory Scores)
Periportal or periseptal interface hepatitis (piecemeal necrosis)
Confluent necrosis;
death of groups of adjacent hepatocytes without clear zonal location
or bridging, zonal confluent necrosis, bridging necrosis linking
vascular structures, and panacinar or multiacinar necrosis.
Focal (spotty) lytic necrosis, apoptosis and focal inflammation;
with liver cell drop-out
Portal inflammation Each of the four histological parameters—periportal or periseptal interface hepatitis (piecemeal necrosis), confluent necrosis, focal (spotty) lytic necrosis, apoptosis and focal inflammation, and portal inflammation—is graded individually on a scoring system using consecutive integers. Comparisons are made between the scores generated for each separate component.

Most patients with CHC have mild or moderate grades of liver necroinflammation. Using the HAI semi-quantitative numerical scoring system, a reduction of at least two points in grading (i.e., necroinflammation) in any component of the HAI is generally considered to be consistent with a medically relevant histological improvement. Similarly, an increase of at least two or more points in grading indicates medically relevant histological worsening.

Although it is methodologically incorrect (Scheuer P J, 1996), a total HAI grading score obtained by summing up the grading components is frequently reported. The sum of the individual scores is the total necroinflammatory score, which ranges from 0 to 18: the higher the score, the more advanced the liver disease. The total HAI grading score is calculated only for comparison with other published studies.

Staging assessed the architectural changes, fibrosis and cirrhosis, on a scoring system using consecutive integers from 0=no fibrosis to 6=probable or definite cirrhosis. Controversy exists in the current practice of defining improvement and/or worsening in staging (fibrosis, cirrhosis). While some consider a change in one point as sufficient, a more conservative approach is to define improvement or worsening based on a change of at least two points.

Clinical Laboratory Evaluation

The following parameters were measured using standard methods:

Haematology: haemoglobin, red cell count, haematocrit, platelet count, white cell count and white cell differential ($\times 10^9$/l)

Biochemistry: sodium, potassium, total calcium, urea (BUN), creatinine, albumin, total protein, bilirubin (total and direct), ALT, alkaline phosphatase, glucose and triglycerides. Triglyceride measurements were to be identified as fasting or non-fasting samples; In the case of abnormal results, measurements were to be repeated using fasting samples.

Urinalysis: glucose, ketones, protein, blood and pH.

Coagulation: prothrombin time.

Thyroid: thyroid-stimulating hormone (if results were abnormal, tests for thyroid microsomal antibodies and for thyroglobulin antibodies would be performed).

Detection of Antibodies to Interferon-beta

Samples for detection of potential antibodies to the study medication were collected at baseline, at the end of Weeks 12, 24 and 48 of treatment and at the end of Week 4 of observation. Guidelines for sample preparation and handling were provided in the study protocol. Samples were first tested for binding antibodies using an enzyme-linked immunoabsorbent assay (ELISA). Test or quality control samples (diluted 1/10) were incubated with antigen (IFN-beta-1a) coated onto microtitre wells. After washing and incubation with a peroxidase-labelled polyclonal antibody to human immunoglobulin and incubation with a chromogenic solution, the optical density (OD) of the resulting coloured solution was measured: the OD is proportional to the concentration of the anti-IFN-beta-1a antibodies present in the sample. A negative control normal human serum sample was included in each assay. The mean OD plus two standard deviations (stds) of the mean was used as the 'cut-off' value to assess the antibody status of the test samples: all samples with OD values below the cut-off value were considered negative. All samples with values above the cut-off were further tested using an absorption assay. This semi-quantitative assay distinguished antibodies binding specifically to IFN-beta-1a from non-specific binding, and provided a titre for the antibodies. Samples positive in the screening ELISA were pre-incubated with fluid-phase antigen (IFN-beta-1a) and were compared directly in the same assay (performed as described above for the ELISA) with non-absorbed samples in a range of dilutions with appropriate controls. A 'cut-off' value was calculated as described for the ELISA, and the OD values of the non-absorbed samples were compared with those of the absorbed samples. Samples that demonstrated a differential in their absorbed vs. non-absorbed OD values were considered positive, and a titre was calculated from the lowest dilution giving an OD value greater than the assay 'cut-off.' Samples that showed no differential between non-absorbed and absorbed OD values were considered negative, as the binding had been shown to be non-specific.

Positive samples then underwent further testing for neutralising activity, using an assay based on the inhibition of the cytopathic effects of vesicular stomatitis virus (VSV) caused by in vitro treatment with human IFN-beta. Human amnion WISH cells, plated in monolayer in 96-well microtitre plates with a mixture of patient serum and a fixed concentration of IFN-beta, were infected with VSV. The number of cells surviving the infection after 24 hours was evaluated by crystal violet staining: the number of surviving cells is proportional to the optical density using an ELISA microplate reader at 592 nm. The greater the amount (titre) of IFN-beta neutralising antibodies in the serum under evaluation, the lesser the protection of the WISH cells from VSV-induced cytopathic effects and consequently, the lower the optical density of the stained monolayer. The quantity of neutralising antibodies is standardised (according to the WHO) in terms of neutralising units (NU) per millilitre. One NU/ml is defined as the amount of neutralising antibody that decreases anti-viral activity from 10 laboratory units (LU) per millilitre to 1 LU/ml (i.e., to the amount of IFN-beta limiting cell damage to 50% of the cytopathic effect induced by the virus in the absence of IFN-beta.) In this study, all samples showing any neutralising activity were considered NAb positive.

Primary and Secondary Efficacy Endpoints

The primary endpoint of the study was the rate of sustained virological response, defined as the absence of detectable HCV RNA in the serum at both the end of treatment (Week 48) and the end of 24 weeks of observation. Secondary endpoints were Presence or absence of HCV RNA in the serum at Week 48 of treatment, Normalisation of serum ALT and ALT values over time, Effect of treatment on viral load, Elimination of HCV RNA and normalisation of ALT as a joint endpoint, and Improvement in liver histology at the end of treatment.

Statistical and Analytical Plans

Study Populations

This study enrolled both cirrhotic and non-cirrhotic patients. The population of non-cirrhotic patients was considered of primary interest, as it was expected to be the primary target population for treatment with IFN-beta-1a.

The safety and efficacy analyses outlined in the following sections were to be performed separately for the cirrhotic and the non-cirrhotic populations. Any comparisons performed between these two populations would be descriptive in nature.

Because of a spontaneous report of good efficacy results by the Investigator in the Taiwanese centre, exploratory analyses by centre and by demographic characteristics were performed, which led to identification of differences between patients of Asian and non-Asian origin. The study's analysis plan was therefore amended to include complete evaluation of these two populations.

Evaluation of Treatment Group Comparability

Baseline characteristics would be tabulated for visual comparison, using summary statistics by treatment group. This would include demographics, medical history, concomitant medications, serum HCV RNA and ALT levels, liver histology and other disease characteristics.

Evaluation of Efficacy

There were to be two interim analyses and one final analysis of the data. The first interim analysis would be performed after completion of 48 weeks of treatment. The second interim analysis would be conducted after the patients involved in the first interim analysis had completed 24 weeks of observation.

Confidence intervals (95%) were to be used at each interim. In addition to univariate tests, the approach suggested by O'Brien (O'Brien P C, 1984) would be used in the final analysis: this is essentially a non-parametric rank-sum test that would test the hypothesis of no treatment difference with power directed towards alternatives in which at least one treatment was uniformly better than the others. Endpoints would be grouped prospectively before the analysis. The results of the interim analyses were to be used for internal planning purposes. They would not be used to alter the course or procedures of the study.

The final analysis would be performed when all patients had completed 48 weeks of treatment and 24 weeks of observation.

Efficacy Analysis Populations

Efficacy analyses for the non-cirrhotic population would be performed using two analysis populations:

All patients (the Intent-to-treat Population)

Patients who completed the study period in question without major protocol violations (the Per Protocol Population)

Intent-to-treat analyses would be performed in two ways: a) considering all dropouts to be treatment failures (primary analysis method) and b) examining detailed causes of dropout. Sensitivity analyses would be performed to compare the results obtained with the two approaches in order to evaluate the robustness of results under different assumptions.

Such detailed analyses would not be performed for the cirrhotic population unless final sample size allowed such analyses.

Statistical Comparisons

Summary statistics would be provided for each endpoint by treatment group. In addition to the analyses performed on the treatment groups, the endpoints would be compared in the following ways:

1) Dose level would be investigated by comparing the responses from patients receiving 44 mcg to those from patients receiving 88 mcg, irrespective of dose regimen.
2) Dose regimen would be investigated by comparing the responses from patients receiving treatment daily to those from patients receiving it three times a week (TIW), irrespective of dose level.
3) Dose-response relationship would be investigated using the planned weekly dose. In case of significant non-compliance, the weekly dose actually received would also be investigated.

Primary Efficacy Endpoint

The primary endpoint of the study was the rate of sustained virological response, defined as the absence of detectable HCV RNA in the serum both at the end of 48 weeks of treatment and at the end of 24 weeks of observation. HCV RNA positivity was considered as non-response. The percentage of responders (response rate) would be calculated per treatment group and compared as outlined below.

Secondary Efficacy Endpoints

The secondary efficacy endpoints were as listed below. Secondary endpoints would be analysed at Week 48 of treatment and Week 24 of observation, unless otherwise specified.

Presence or absence of HCV RNA in the serum at Week 48 of treatment.

ALT normalisation and ALT values over time.

Effects of treatment on viral load, including change in serum HCV RNA and percent change in serum HCV RNA concentrations.

Elimination of HCV RNA and normalisation of ALT as a joint endpoint.

Improvement in liver histology (grade and stage) at the end of treatment as compared to the pretreatment biopsy. Histological grading would be based on the semi-quantitative Knodell Histological Activity Index (HAI), modified according to Ishak et al. The modified HAI scoring system includes four separate components for grading necroinflammatory activity. Comparisons would be made between the scores generated for each separate component. Although it is methodologically incorrect (Sheuer P J, 1996), a total HAI grading score obtained by summing up the grading components is frequently reported. The total HAI grading score would therefore be calculated for comparison with other published studies. Histological staging, assessing architectural changes, fibrosis and cirrhosis, would be based on a separate staging scale as published by Ishak et al.

Statistical Methodology

The endpoints in this study included binary outcomes, categorical outcomes with more than two levels and continuous outcomes Therefore, the following methodologies were to be used. Stratification by centre would be performed if sufficient numbers of patients were enrolled per centre. Because of the low numbers of cirrhotic patients per centre, it was not planned to take centre into account in the analyses of the cirrhotic population, but otherwise the same methodology would be used for the cirrhotic and non-cirrhotic populations.

Response rates based on binary endpoints (such as elimination of HCV RNA) would be compared between treatment groups using one-sided Fisher's exact tests with a significance level of 0.05, and would be stratified by centre if feasible.

Exploratory analyses to investigate the effect of covariates on binary outcomes would be performed using logistic regression, including a term for centre if feasible. The results from these analyses would therefore be asymptotic and not exact.

Response rates based on categorical endpoints (such as grading and staging) would be compared between treatment groups using Mantel-Haenszel tests (row mean scores), stratified by centre if feasible.

Individual profiles of continuous measures (HCV RNA and ALT) assessed repeatedly over time would be plotted in order to determine which measure was a suitable summary of the response for all patients.

Continuous efficacy endpoints (such as change in HCV RNA) would be analysed using analysis of variance (ANOVA; main effect model, including factors for treatment and centre). Dose-response relationship would be investigated with a test for trend (Cuzick J, 1985) as well as differences between received and planned doses.

Continuous safety endpoints (such as laboratory values) would be analysed using Wilcoxon signed-rank tests (to verify significant changes from baseline) and Kruskal-Wallis tests (to verify treatment heterogeneity), which would not include a factor for centre.

The correlation between primary and secondary endpoints would be analysed with a descriptive and exploratory aim. Separate plots would be given for each dose level and regimen.

Results for endpoints measured at different times (such as Week 48 of treatment and Week 24 of observation) would be displayed accordingly.

Determination of Sample Size

A sample size of 50 non-cirrhotic patients per treatment group was chosen based on clinical considerations. Fisher's exact test was used to compare percentages of responders (patients without detectable HCV RNA) because of the small sample sizes involved and the correspondingly small expected cell frequencies in the table of outcome versus treatment. Sample sizes and power estimated from formulas for the two-group, continuity-corrected $X^2$ test of equal proportions were appropriate for use with Fisher's exact test. There were provisions for the enrolment of approximately 50 cirrhotic patients who would be randomised to the four treatment groups and distributed equally among the centres. The number of cirrhotic patients to be enrolled per centre was limited in order to ensure a total of approximately 50. Study enrolment was to be stopped based on the enrolment of the desired number of non-cirrhotic patients.

Changes in the Conduct of the Study or Planned Analyses

Because of a spontaneous report of good efficacy results by the Investigator in the Taiwanese centre, preliminary exploratory analyses of main efficacy endpoints by centre (Taiwanese and other) and by demographic characteristics (Asian vs. non-Asian race) were performed before database lock. The analysis plan for the study was updated based on the results of these preliminary analyses and those of the first interim analysis, which showed complete virological response at Week 48 in very few patients and few differences between cirrhotic and non-cirrhotic populations. Changes to the original analysis plan included:

Efficacy would be assessed using only the Full Analysis Set (the Intent-to-treat population, including all randomised patients who received any study drug).

No statistical hypothesis tests would be performed on the primary efficacy variable (the rate of sustained virological response).

Efficacy analysis would be mainly descriptive, with estimation of 95% confidence intervals where appropriate.

Subgroup analyses of Asian and non-Asian populations would be performed for baseline characteristics and for efficacy and safety endpoints.

The main analysis of the primary efficacy endpoint would Involve estimation of confidence intervals for the percentages of patients showing sustained virological response: hypothesis tests would not be meaningful because of the very low numbers of responses observed. Effects of treatment, cirrhotic status, Asian origin and baseline HCV RNA would also be investigated using mainly descriptive methods, and the effect of other covariates including age, sex and treatment exposure would be explored.

For secondary efficacy endpoints, 95% confidence intervals would be calculated. For binary variables, the exact binomial distribution would be used. For continuous variables that did not match the assumption of normality, non-parametric confidence intervals would be calculated for the median (confidence intervals would be 95% nominally).

Presence or absence of HCV RNA in the serum at Week 48 of treatment would be summarised by the 'virological clearance rate' (the number of patients with no HCV RNA detected divided by the number of randomised and treated patients).

ALT normalisation would be summarised by the 'normalisation rate' (the number of patients with normal ALT divided by the number of randomised and treated patients), and ALT values over time would be summarised using descriptive statistics.

Effects of treatment on viral load would be examined using descriptive statistics for measured values and assessment of absolute and percent changes in serum HCV RNA concentrations.

Elimination of HCV RNA and normalisation of ALT as a joint endpoint would be assessed by examining the numbers and percentages of patients having both HCV RNA clearance and ALT normalisation at Week 48 of treatment and at Week 24 of observation.

Improvement in liver histology would be assessed using the Knodell Histological Activity Index (HAI), modified according to Ishak et al. Four components for grading necroinflammatory activity and one score for staging fibrosis/cirrhosis would be evaluated. Change would be assessed by subtracting baseline scores from Week 48 scores, with a negative result indicating improvement. Scores and changes for each component would be summarised using frequency counts. The total HAI grading score would be obtained by summing the four component scores for each patient and would be summarised using descriptive statistics (considering the total score as a continuous variable). Improvements in staging components would be analysed using logistic regression (or a Cochran-Mantel-Haenszel test if sample sizes were too small) to investigate the effect of demographic and baseline characteristics, and confidence intervals would be calculated for the odds ratios.

Inferential analyses (Fisher's exact test and logistic regression) were employed in an exploratory manner to generate hypotheses, notably In relation to differences between Asian and non-Asian patients. It should be noted that there was a very large imbalance between the numbers of Asian and non-Asian patients. Therefore, caution is required in the interpretation of results of inferential analyses.

Fisher's exact test was used to compare the proportions of Asian and non-Asian patients achieving HCV RNA clearance (at week 48 of treatment and Week 24 of observation), sustained HCV RNA clearance, ALT normalisation at Week 12, ALT normalisation at Week 24 and sustained ALT normalisation. Ninety-five percent confidence intervals for the proportions were calculated using the exact method of Armitage and Berry (Armitage P, 1990). Unadjusted odds ratios for Asian versus non-Asian populations were calculated, together with their 95% confidence i ntervals.

Logistic regression (SAS Proc Logistic) was used to assess the influence of selected potential explanatory variables on the main efficacy endpoints: sustained HCV RNA clearance, complete HCV RNA clearance (at Week 48) and sustained ALT normalisation. The explanatory variables employed were the baseline values of the endpoint variables (e.g., baseline HCV RNA), age, sex, cirrhotic status, race (Asian vs. non-Asian), treatment regimen (4 groups), dose frequency (TIW vs. QD), dose intensity (44 mcg vs. 88 mcg) and exposure (total dose and dose/kilogram). Forward selection was employed for the inclusion of variables in the model. Adjusted and unadjusted odds ratios were calculated.

DISPOSITION OF PATIENTS

Analyses included in this section were performed for five populations of patients: the total population, the cirrhotic and non-cirrhotic subgroups, and the Asian and non-Asian subgroups. A total of 270 patients were enrolled and randomised in the 19 centres. Of these patients, 43 were randomised as cirrhotic and 227 were randomised as non-cirrhotic. Twenty-four (24) of the 270 patients (8.9%). enrolled in 4 centres, were of Asian background. Two of the Asian patients were randomised as cirrhotic and the others were randomised as non-cirrhotic.

A total of 65 patients were randomised to 44 mcg TIW, 68 were randomised to 88 mcg TIW, 72 were randomised to 44 mcg QD and 65 were randomised to 88 mcg QD. Among the Asian subgroup, 6 patients were randomised to each TIW treatment group, 5 were randomised to 44 mcg QD and 7 were randomised to 88 mcg QD.

Three randomised patients never received treatment and are omitted from all the following Tables. All three of these patients were non-Asian.

One patient was excluded from efficacy analyses because central assessment of HCV RNA by PCR at baseline showed him to be HCV-negative: this patient was entered into the study on the basis of an HCV RNA test performed by a local laboratory, which was positive. This patient should have been excluded from the study because of the negative central laboratory result; however, as this result was not available until he had already received treatment, it was decided to include him in pre-study and safety analyses.

Overall, 198 of the 267 randomised patients completed 48 weeks of treatment (74.2%), and 183 completed both the treatment and the observation periods (68.5%).

Fifty-six (56) patients dropped out before completing the treatment period. The pattern of early withdrawals clearly indicated regimen-related limitations of patient compliance and tolerability: 43 of 56 dropouts had been receiving daily administration of treatment.

Thirty-two of 43 cirrhotic patients completed treatment (74.4%), 31 of which went on to complete the observation period (72.1% of the population). Of the 9 cirrhotic patients who dropped out of the treatment phase, 5 were receiving daily dosing.

Twenty-one (21) of the 24 Asian patients completed 48 weeks of treatment (87.5%), and all of these patients went on to complete the observation period. Dropouts in this population did not show a clear relation to dose or frequency of administration; however, there were only two dropouts.

The completion rate among Asian patients was noticeably higher than that among non-Asians: 87.5% completed the treatment period compared to 72.8% (177 of 243) for non-Asians, and 87.5% completed both treatment and follow-up compared to 66.7% (162 of 243) for non-Asians.

FIGS. 1 to 3 illustrates the patient's disposition according to the study object of the present invention.

EFFICACY EVALUATION

Data Sets Analysed

Efficacy analyses were to be performed using the Full Analysis Set (Intent-to-treat), consisting of all randomised patients who received at least one dose of study drug. However, one patient (non-cirrhotic and Asian) was excluded from efficacy analyses because central assessment of HCV RNA by PCR at baseline showed him to be HCV-negative (an HCV RNA assay performed by a local laboratory had shown him to be HCV RNA positive). This patient should have been excluded from the study based on the central laboratory result; however, as this result was not available until he had received treatment, it was decided to include him in pre-study and safety analyses.

All analyses included in this section were performed for five populations of patients: the total population, the cirrhotic and non-cirrhotic subgroups, and the Asian and non-Asian subgroups. Comparative tabulations were also prepared presenting results for both the Asian and the non-Asian subgroups. Results focus on the total population, the Asian subgroup, and the comparison of the Asian and non-Asian subgroups. Demographic and Other Baseline Characteristics Where measurements were made several times before the initiation of study treatment, those measured on Study Day 1 before study drug administration were taken as baseline measurements. If Study Day 1 measurements were not available, the pre-study measurements taken closest to Study Day 1 were used.

Demographics

Table 2 presents demographic characteristics for the various populations. The population as a whole was predominantly white (81.3%) and male (74.9%). These proportions did not differ appreciably between treatment groups, or between cirrhotic and non-cirrhotic populations. Among the Asian subgroup, the proportion of men was somewhat lower (66.7%).

Age, height, weight, and body mass index (BMI) were generally similar across treatment groups in the total population. In the cirrhotic subgroup, the 44 mcg TIW patients were slightly older than those In the other treatment groups, with slightly lower weight and BMI. In the Asian subgroup differences between treatments in age, height, weight and BMI were more marked.

Asian patients were smaller and lighter than non-Asians, but age was similar between these two sub-populations. Cirrhotic patients were slightly older and heavier than non-cirrhotic patients.

TABLE 2

Demographics (Asian vs. Non-Asian Populations)

| | Demographics | Asian (n = 24) | Non-Asian (n = 243) | Total (n = 267) |
|---|---|---|---|---|
| Age (years) | Number | n = 24 | n = 243 | n = 267 |
| | Mean (std) | 47 (12.2) | 44.9 (8.1) | 45.1 (8.6) |
| | Median (Q1; Q3) | 44.5 (38; 59.5) | 45 (40; 50) | 45 (39; 50) |
| | Range | 23; 64 | 16; 69 | 16; 69 |
| Weight (kg) | Number | n = 24 | n = 243 | n = 267 |
| | Mean (std) | 68.5 (10.4) | 85.8 (19.3) | 84.3 (19.3) |
| | Median (Q1; Q3) | 68 (63; 76.5) | 84 (73.2; 96) | 81 (71.4; 95) |
| | Range | 46; 86 | 47; 162 | 46; 192 |
| Height (cm) | Number | n = 24 | n = 243 | n = 267 |
| | Mean (std) | 165.3 (7.5) | 172.7 (9.) | 172.1 (9.9) |
| | Median (Q1; Q3) | 167 (160; 172) | 173 (166; 180.3) | 172.7 (165.1; 180) |
| | Range | 151; 178 | 149; 202 | 149; 202 |
| BMI ($kg/m^2$) | Number | n = 24 | n = 243 | n = 267 |
| | Mean (std) | 25 (3.5) | 28.7 (5.7) | 28.4 (5.7) |
| | Median (Q1; Q3) | 25.1 (22.7; 27.4) | 28.4 (24.7; 31.2) | 27.9 (24.5; 30.9) |
| | Range | 18; 33 | 17; 58 | 17; 58 |
| Sex | Male | 16 (66.7%) | 184 (75.7%) | 200 (74.9%) |
| | Female | 8 (33.3%) | 59 (24.3%) | 67 (25.1%) |

Duration and Mode of Infection

Overall, duration of infection ranged from 7 to 374 months, with a mean (±std) of 63 (±57) months and a median of 46.5 months. Not surprisingly, mean and median disease duration were longer among cirrhotic than among non-cirrhotic patients. The duration of infection was shorter among Asians than among non-Asians: mean (±std) and median for Asians were 41.3 (±19.7) and 34 months, compared to 64.8 (±58.7) and 47.5 months for non-Asians. This difference was not statistically significant (p=0.077).

The most frequent mode of transmission reported was IV drug abuse (109 of 267 patients; 40.8%), followed by 'unknown' and blood transfusion. Among cirrhotic patients, IV drug abuse was most common, followed by blood transfusion and 'unknown.' Among Asians, the only modes of transmission reported were blood transfusion (one patient) and 'unknown' (23 patients).

Previous IFN-alpha Therapy

Close to two thirds of patients received IFN-alpha-2b as their most recent interferon-alpha therapy before study entry. IFN-alpha-2a was the second most commonly prescribed therapy. The most common regimen was 3 MIU given subcutaneously 3 times a week. Therapy choices were consistent across treatment groups in the total, cirrhotic, non-cirrhotic and non-Asian populations. Among Asians, equal numbers of patients had received IFN-alpha-2a and IFN-alpha-2b; however, the most common regimen in this population was also 3 MIU subcutaneously 3 times a week.

Mean treatment duration for the previous IFN alpha therapy was approximately 6 months for all populations except Asians, for whom mean duration was approximately 5 months. Treatment durations of less than 3 months are most likely 'artefacts' due to the data collection convention applied in this study: according to which a change in dose or frequency of injection was considered the beginning of a new treatment course. Overall, 22.8% of patients had undergone more than one interferon-alpha treatment before study entry; this proportion was generally consistent across populations.

As expected, the ALT serum concentration at the end of IFN-alpha therapy was reported as abnormal for all patients but one, and only two patients showed HCV RNA clearance (HCV RNA results were only available for 140 patients).

Overall, HCV RNA levels ranged between 0.2 and 127.8× $10^6$ mEq/ml: mean (±std) and median values were 12.4 (±15.4) and 7.4×$10^6$ mEq/ml, respectively. HCV RNA levels were somewhat lower among cirrhotic patients than among non-cirrhotic patients: mean (±std) and median were 10.2 (±15.8) and 4.7×$10^6$ mEq/ml for cirrhotic patients compared to 12.8 (±15.3) and 8.5×$10^6$ mEq/ml for non-cirrhotics.

Asians presented with lower HCV RNA levels than non-Asians, with a mean (±std) and median of 5 (±6.2) and 2.6×$10^6$ mEq/ml for Asians compared to 13.1 (±15.8) and 8.7×$10^6$ mEq/ml for non-Asians. This difference was statistically significant (p<0.001). The maximum value among Asians was only 23.2×$10^6$ mEq/ml.

HCV Genotyping

Six (6) main genotypes of the hepatitis C virus are currently recognised, many of which contain more closely related variants, so-called subtypes. Some genotypes of HCV, such as subtypes 1a, 2a and 2b, show a broad worldwide distribution, while others such as types 5a and 6 are found only In specific geographical regions. In Western Europe and the USA, genotypes 1a, 1b, 2a, 2b and 3a are observed frequently in patients with CHC. Genotypes 3 and 6 are widespread in India and Southeast Asia.

Hepatitis C virus genotype 1 is considered a negative prognostic indicator for expected response to interferon-based treatments (McHutchison J G et al., 1998; In Poynard T et al., 1998). Since this study included a patient population of interferon-alpha non-responders, it was reasonable to expect a higher percentage of patients expressing genotype 1 than in the normal HCV-infected population. However, this was not the case. In the non-Asian population, the prevalence of the various hepatitis C virus genotypes (81.5% genotype 1) was consistent with the actual prevalence of genotypes reported in the United States (Alter M J et al., 1999; Zein N N et al., 1996) and Europe (McOmish F et al., 2000). Type 1 is also the predominant genotype for Asia, particularly in Japan and China, while genotype 6 is seen predominantly in Hong Kong. The type 3 genotype is seen in some areas of Southeast Asia, particularly in Thailand, but also in Australia and New Zealand (McCaughan G W, 2000).

As might be expected, the distribution of genotypes differed between the Asian and non-Asian populations. In the Asian population, genotype 1 was found in 12 of 24 patients (50%). Ten (10) patients (43.5%) were infected with HCV genotype 2 and one patient (4.3%) was infected with genotype 6.

In the non-Asian population, 198 of 243 patients expressed genotype 1, 1a, 1a/b or 1b (81.5%). Non-1 genotypes observed were 2, 3, 3a, 4, 4c/d and 5.

Distribution of genotypes did not differ substantially among treatment groups.

EFFICACY RESULTS

When interpreting efficacy data, especially concerning dose-relationship, the pattern of early withdrawals across the four treatment groups should be kept in mind (discussed in section 0); low discontinuation rates for the TIW regimen versus high rates for the QD groups clearly indicated that patient compliance and tolerability limits were being reached. Because of the increased dropout rates in the QD dose groups, any conclusions drawn for these groups apply to small, selected (and possibly biased) patient populations.

In general, few differences were observed between the cirrhotic and non-cirrhotic populations; however, differences between Asians and non-Asians were often striking. The size of the cirrhotic and Asian subgroups (n=43 and n=24) should be considered, as this may limit the ability to generalise results.

Primary Endpoint: Rate of Sustained Virological Response

Sustained virological response was defined as the absence of detectable HCV RNA in the serum at both the end of treatment (Week 48) and the end of 24 weeks of observation: there were no HCV RNA measurements between these time points.

Table 3 presents patient numbers and rates of sustained virological clearance, with confidence intervals for the rates. Rates of sustained virological response were low overall: a total of 9 sustained responses were noted, representing a response rate of 3.4% for the total population. In the cirrhotic subgroup, only one sustained response was noted (a response rate of 2.3%), in an Asian patient receiving 44 mcg TIW.

In the Asian subgroup, however, sustained response rates were markedly higher than those in the total and the non-Asian populations: 5 of the 9 sustained responses occurred in Asian patients. The response rate among Asians was 21.7% (5 of 23 patients) compared to only 1.6% for non-Asians: the confidence intervals do not overlap providing evidence of a significant difference. Response rates by treatment group ranged from 16.7% to 28.6% among Asian patients and appeared to be dose- and frequency-related, although numbers of patients concerned were very small.

The apparent dose-response relationship seen in the Asian subgroup was also present in the total population, in which response rates by treatment group ranged from 1.5% to 6.3%. However, confidence intervals for the sustained response rates overlapped one another, indicating that the observed relationship was not statistically significant.

TABLE 3

Sustained HCV RNA Clearance and 95% CI for the Rate (Asian vs. Non-Asian Populations)

| Sustained Response | Asians (n = 23) | Non-Asians (n = 243) | Total (n = 266) |
|---|---|---|---|
| No | 18 - 78.3% (56.3; 92.5) | 239 - 98.4% (95.8; 99.5) | 257 - 96.6% (93.7; 98.4) |
| Yes | 5 - 21.7% (7.5; 43.7) | 4 - 1.6% (0.5; 4.2) | 9 - 3.4% (1.6; 6.3) |

For patients who achieved sustained virological response, time to sustained response was examined using the definition of time between the start of treatment and the first observed HCV RNA clearance (Table 4). Sustained clearance was achieved after one to 48 weeks of treatment. Asian patients showed HCV RNA clearance earlier than non-Asian patients, after one to 4 weeks of treatment compared to 11 to 48 weeks for non-Asians.

TABLE 4

Time to Sustained HCV RNA Clearance (Total Population)

| Patient* | Treatment | Time to Sustained Clearance (weeks) |
|---|---|---|
| 91420091027 (NC-A) | 88 mcg QD | 4 |
| 91420231005 (NC-A) | 88 mcg QD | 2 |
| 91420231008 (NC-A) | 88 mcg TIW | 1 |
| 91420231017 (NC-A) | 44 mcg QD | 2 |
| 91420232013 (C-A) | 44 mcg TIW | 2 |
| 91420041009 (NC-NA) | 44 mcg QD | 47 |
| 91420091029 (NC-NA) | 88 mcg TIW | 12 |
| 91420151007 (NC-NA) | 88 mcg QD | 48 |
| 91420161002 (NC-NA) | 88 mcg QD | 11 |

*In parentheses: C = cirrhotic, NC = non-cirrhotic, A = Asian, NA = non-Asian.

This observation can be used to set up a "test-phase" during which HCV patients undergo the treatment with IFN-beta: the patients who, after a period going from 1 to 4 weeks of treatment, will show HCV RNA clearance will have a very high probability (close to 100%) to achieve at the end of treatment a sustained response.

Secondary Endpoints

Complete HCV RNA Response at Week 48

The protocol-defined endpoint of 'presence or absence of HCV RNA in the serum at Week 48' examined the complete clearance of HCV RNA from the serum (complete HCV RNA response).

Table 5 presents complete HCV RNA response rates for the various populations with confidence intervals. A total of 22 patients showed complete HCV RNA response at Week 48 (8.3% of the total population). Complete response rates were similar In the cirrhotic, non-cirrhotic and non-Asian populations (7.0%, 8.5% and 6.6% respectively). Response appeared to be dose-related in the total, non-cirrhotic and non-Asian populations: from 4.6% to 14.3% in the total population, 1.8% to 17.0% in the non-cirrhotic population and 1.7% to 12.5% in the non-Asian population.

Asians accounted for 6 of the 22 complete responses at Week 48, demonstrating a complete response rate of 26.1% compared to 6.6% for non-Asians. A dose relation could not be established in the Asian population, possibly due to the small numbers of patients; the highest response rate occurred in the group receiving the lowest dose (44 mcg TIW; 2 of 6 or 33.3%).

TABLE 5

Complete HCV RNA Response and 95% CI for the Rate (Asian vs. Non-Asian Populations)

| Response | Asians (n = 23) | Non-Asians (n = 243) | Total (n = 266) |
|---|---|---|---|
| No | 17 - 73.9% (51.6; 89.8) | 227 - 93.4% (89.5; 96.2) | 244 - 91.7% (87.7; 94.7) |
| Yes | 6 - 26.1% (10.2; 48.4) | 16 - 6.6% (3.8; 10.5) | 22 - 8.3% (5.3; 12.3) |

In the total population, a peak in the percentage of patients showing clearance occurred at Week 12 (13.9% of patients with HCV RNA clearance). After this time, the percentage decreased.

The cirrhotic population showed the maximum percentage of patients with HCV RNA clearance at Week 4, but patterns in individual treatment groups differed (the 44 mcg TIW group showed an increase at Week 4, the 44 mcg QD group at Weeks 12 and 24, and the numbers of responses in the other groups were too small to show any pattern).

In the Asian population, the peak occurred at Week 4. As with the cirrhotic population, different treatment groups showed different patterns, with increases noted at Week 24 for 44 mcg TIW, Week 2 for 88 mcg TIW, Week 12 for 44 mcg QD and Week 4 for 88 mcg QD.

In the total population, 56 patients showed clearance of HCV RNA at least once (21.1%). Among cirrhotic patients 18.6% showed clearance at least once compared to 21.5% for non-cirrhotics. Among Asian patients, 13 showed at least one clearance of HCV RNA (56.5%, compared to 17.7% for non-Asians; confidence Intervals did not overlap, providing evidence of a significant difference). Percentages of patients showing at least one clearance increased with dose and frequency of administration in all populations but the cirrhotic subgroup, in which no pattern was clear.

Normalisation of Serum ALT at the End of Treatment

It should be noted that Asian patients had higher ALT values at Day 1 than non-Asians: mean (±std) and median for Asians were 200.6 (±145.4) and 150 IU/l, compared to 137.3 (±88.4) and 106.5 IU/l for non-Asians. This difference was statistically significant (p=0.023).

Table 6 presents numbers and percentages of patients showing normalisation of serum ALT at the end of treatments with confidence intervals. In the total population, 46 patients showed ALT normalisation at Week 48 (17.3%). Rates of ALT normalisation at Week 48 were slightly lower for cirrhotic patients compared to non-cirrhotic patients (11.6% compared to 18.4%), and Asians fared notably better than non-Asians (26.1% compared to 16.5%). There was no clear relation between ALT response and dose or frequency of administration.

TABLE 6

Normalisation of ALT at the End of Treatment (Asian vs. Non-Asian Populations)

| Normalisation | Asians (n = 23) | Non-Asians (n = 243) | Total (n = 266) |
|---|---|---|---|
| No | 17 - 73.9% (51.6; 89.8) | 203 - 83.5% (78.3; 88.0) | 220 - 82.7% (77.6; 87.1) |
| Yes | 6 - 26.1% (10.2; 48.4) | 40 - 16.5% (12.0; 21.7) | 46 - 17.3% (12.9; 22.4) |

In the total population, 37 patients showed normal serum ALT at the end of the observation period (13.9%; down from 17.3% at the end of treatment). The highest percentage of patients with normal serum ALT was seen in the 88 mcg QD group (20.6%); percentages in the other treatment groups ranged from 10.8% to 13.4%.

Among cirrhotic patients, only 4.7% showed normal ALT at the end of observation (2 patients, one receiving 44 mcg TIW and the other 44 mcg QD compared to 15.7% for non-cirrhotics. Corresponding percentages at the end of treatment were 11.6% for cirrhotic and 18.4% for non-cirrhotic patients.

Among non-Asians, 9.9% showed normal ALT at Week 24 of observation compared to 16.5% at the end of treatment; however, the normalisation rate among Asians had actually increased, from 26.1% at the end of treatment to 56.5% at the end of observation.

The difference between Asians and non-Asians at Week 24 of observation was significant as demonstrated by non-overlapping confidence intervals. Response appeared to be better with higher doses in the Asian population, but confidence intervals overlapped (see Table 7).

TABLE 7

Normalisation of ALT at Week 24 of Observation (Asian vs. Non-Asian Populations)

| Normalisation | Asians (n = 23) | Non-Asians (n = 243) | Total (n = 266) |
|---|---|---|---|
| No | 10 - 43.5% (23.2; 65.5) | 219 - 90.1% (85.7; 93.6) | 229 - 86.1% (81.3; 90.0) |
| Yes | 13 - 56.5% (34.5; 76.8) | 24 - 9.9% (6.4; 14.3) | 37 - 13.9% (10.0; 18.7) |

Sustained normalisation was defined as ALT values within the normal range at both Week 48 and Week 24 of observation without abnormal results between these two measurements. Sustained normalisation was noted in only 14 patents in the total population (5.3%). There was no apparent dose effect, but the numbers of patients concerned were small.

Only one cirrhotic patient (assigned to 44 mcg QD) achieved sustained normalisation of ALT (2.3%, compared to 5.8% for non-cirrhotics.

Four (4) of the 14 patients showing sustained ALT normalisation were Asian, for a normalisation rate of 17.4% for Asians compared to 4.1% for non-Asians. Two (2) of the 4 Asian responders were receiving 44 mcg QD and the others were receiving 88 mcg TIW.

Effect of Treatment on Viral Load

Discussion of viral load concerns HCV RNA values by visit and changes from baseline for different groups of patients: 'baseline' was defined as the value measured before treatment on Day 1 where this was available and the pre-study value measured closest to Day 1 otherwise.

In the total population, baseline viral load varied widely, from 0.2 to 127.8×10$^6$ mEq/ml at Day 1. Median values at baseline varied slightly between treatment groups (from 6.0 to 10.2×10$^6$ mEq/ml at Day 1). Decreases in viral load were evident as early as Day 3 (the first on-treatment measurement), and minimum values were reached by Week 4. There was no clear dose effect, although decreases in viral load were consistently greater in patients receiving 88 mcg (either TIW or QD). After Week 4, HCV RNA gradually increased, reaching levels near baseline in all treatment groups by Week 24 of observation.

Baseline viral load was somewhat lower for cirrhotic patients than for non-cirrhotics: median values were 4.7×10$^6$ mEq/ml at Day 1 for cirrhotic patients, compared to 12.8×10$^6$ mEq/ml for non-cirrhotic patients. Variation between treatment groups at baseline was more pronounced among cirrhotics than among non-cirrhotics: median values at Day 1 ranged from 1.6 to 10.2×10$^6$ mEq/ml among cirrhotics, compared to 10.9 to 15.2×10$^6$ mEq/ml among non-cirrhotics. This finding is most likely due to the smaller numbers of cirrhotic patients. Changes from baseline among cirrhotic patients followed the same general pattern seen in the total population: prompt decreases reaching a maximum between Weeks 4 and 12 and returning gradually to baseline thereafter. There was no clear relation between response and dose, though again decreases were greater for patients receiving 88 mcg.

Median viral load at baseline was notably lower for Asians than for non-Asians (2.6×10$^6$ mEq/ml at Day 1 compared to 8.7×10$^6$ mEq/ml for non-Asians). The range of baseline values was also smaller for Asians (0.2-23.2×10$^6$ mEq/ml at Day 1 compared to 0.2-127.8×10$^6$ mEq/ml for non-Asians). This difference was statistically significant (p<0.001). Baseline variation between treatment groups was somewhat greater in the Asian than in the non-Asian population (medians ranged from 0.6 to 5.7×10$^6$ mEq/ml on Day 1 for Asians and from 6.1 to 10.5×10$^6$ mEq/ml for non-Asians), probably due to the small numbers of Asian patients. As seen in the other populations, viral load decreased promptly In the Asian population, reaching a maximum between Weeks 4 and 12 and returning to baseline by Week 24 of observation. There was no clear relation between response and dose.

Among sustained responders, the range of baseline values was smaller and lower than for the population as a whole (in the total population, 0.2-17.7×10$^6$ mEq/ml at Day 1 for sustained responders compared to 0.2-127.8×10$^6$ mEq/ml for all patients).

As observed for the full population, decreases were seen early (Day 3), generally reaching greatest magnitude (in the case of sustained responders, complete HCV RNA clearance) after 2 to 12 weeks of treatment.

There was only one sustained responder in the cirrhotic population. This patient's baseline value was 0.2×10$^6$ mEq/ml, which decreased to zero after two weeks of treatment and remained there.

Five (5) of the 9 sustained responses occurred in the Asian population. Median baseline values varied between treatment groups among both Asian and non-Asian sustained responders: from 0.2 to 7.8×10$^6$ mEq/ml for Asians (medians were less than or equal to 1×10$^6$ mEq/ml in all treatment groups but 88 mcg QD) and from 1.9 to 17.7×10$^6$ mEq/ml for non-Asians at Day 1. Overall median values at Day 1 were 1×10$^6$ mEq/ml for Asian sustained responders and 3×10$^6$ mEq/ml for non-Asians. Four (4) out of 5 Asian sustained responders had undetectable viral loads by Week 2: the remaining patient achieved clearance by Week 4. In non-Asian sustained responders, decreases in HCV RNA occurred early (Day 3) but complete clearance was not achieved until Week 11 (one patient) or Week 48 (3 patients).

Elimination of HCV RNA and Normalisation of ALT (as Joint Endpoint)

Table 8 presents numbers and percentages of patients with both HCV RNA clearance and ALT normalisation at the end of the treatment period, with confidence intervals. In the total population, only 10 patients showed both HCV RNA clearance and ALT normalisation at Week 48 (3.8%): these patients were distributed evenly across the 88 mcg TIW, 44 mcg QD and 88 mcg QD groups. No cirrhotic patients achieved both endpoints. Two (2) of the combined responders were Asian, for combined response rates of 8.7% for Asians and 3.3% for non-Asians.

TABLE 8

Response in Terms of Both HCV RNA and ALT Normalisation at Week 48 of Treatment (Asian vs. Non-Asian Populations)

| Both Responders | Asians (n = 23) | Non-Asians (n = 243) | Total (n = 266) |
| --- | --- | --- | --- |
| No | 21 - 91.3% | 235 - 96.7% (93.6; 98.6) | 256 - 96.2% (93.2; 98.2) |
| Yes | 2 - 8.7% (1.1; 28.0) | 8 - 3.3% (1.4; 6.4) | 10 - 3.8% (1.8; 6.8) |

Table 9 presents numbers and percentages of patients showing both sustained clearance of HCV RNA (clearance at both Week 48 and Week 24 of observation) and normalisation of ALT at Week 24 of observation, with confidence intervals. In the total population, only 8 patients achieved both endpoints (3.0%). Two (2) of these patients were receiving 88 mcg TIW, 2 were receiving 44 mcg QD and 4 were receiving 88 mcg QD. None of the combined responders was cirrhotic. Notably, 4 of the combined responders were Asian, leading to combined response rates of 17.4% for Asians and 1.6% for non-Asians.

Interestingly, the percentage of Asian patients showing combined response at Week 24 of observation (defined by normal ALT at Week 24 of observation and sustained HCV RNA clearance) was higher than the percentage with combined response at the end of treatment at Week 48, while the percentage of non-Asians with combined response was lower at Week 24 of observation than at Week 48.

TABLE 9

Response in Terms of Both HCV RNA Sustained Clearance and ALT Normalisation at Week 24 of Observation (Asian vs. Non-Asian Populations)

| Both Responders | Asians (n = 23) | Non-Asians (n = 243) | Total (n = 266) |
| --- | --- | --- | --- |
| No | 19 - 82.6% (61.2; 95.0) | 239 - 98.4% (95.8; 99.5) | 258 - 97.0% (94.2; 98.7) |
| Yes | 4 - 17.4% (5.0; 38.8) | 4 - 1.6% (0.5; 4.2) | 8 - 3.0% (1.3; 5.8) |

Results of Exploratory Analyses

Inferential analyses (Fisher's exact test and logistic regression) were employed in an exploratory manner to generate hypotheses, notably in relation to differences between Asian and non-Asian patients. It should be noted that there was a very large imbalance between the numbers of Asian and non-Asian patients. Therefore, caution is required in the interpretation of results of inferential analyses.

Fisher's Exact Test

Fisher's exact test was used to compare the proportions of Asian and non-Asian patients achieving HCV RNA clearance (at week 48 of treatment and Week 24 of observation), sustained HCV RNA clearance, ALT normalisation at Week 12, ALT normalisation at Week 24 and sustained ALT normalisation. Ninety-five percent confidence intervals for the proportions were calculated using the exact method of Armitage and Berry. Unadjusted odds ratios for Asian versus non-Asian populations were calculated, together with their 95% confidence intervals. Comparisons of main efficacy results between Asian and non-Asian patients are presented in FIG. 4 for endpoints associated with HCV RNA clearance and in FIG. 5 for those associated with ALT normalisation. In each figure, the dots represent the percentage of patients in each population who achieved the endpoint and the horizontal lines represent confidence intervals for these percentages; unadjusted odds ratios (OR) and confidence intervals (CI) for these odds ratios are also presented.

Although the number of Asian patients was relatively small, Asians were significantly more likely than non-Asians to achieve complete HCV RNA clearance at Week 48 of treatment (unadjusted OR 5.0; CI for odds ratio [1.7-14.5]; p=0.006), at Week 24 of observation (unadjusted OR 8.2; CI for odds ratio [2.4-27.5]; p=0.003) and at both time points (sustained virological response, the primary efficacy endpoint of the study: unadjusted OR 16.6; CI for odds ratio [4.1-67.3]: p<0.001).

Asians were also more likely than non-Asians to have normal serum ALT: the difference was not statistically significant at Week 48 of treatment (unadjusted OR 1.8; CI for odds ratio [0.7-4.8]; p=0.251), but at Week 24 of observation the unadjusted odds ratio for Asians vs. non-Asians was 11.9 (CI for odds ratio [4.7-29.9]; p<0.001), and the unadjusted odds ratio for Asians vs. non-Asians for sustained ALT normalisation was 4.9 (CI for odds ratio [1.4-17.11; p=0.024).

FIG. 4 illustrates the Endpoint Summary relating to HCV RNA Clearance (Asian vs. Non-Asian Populations).

FIG. 5 illustrates the Endpoint Summary relating to ALT Normalisation (Asian vs. Non-Asian Populations).

EFFICACY SUMMARY

The three classical endpoints employed in studies of antiviral therapy for CHC are ALT normalisation, HCV RNA clearance and improvement in liver histology. Improvements in the assay technology allowing for the detection of HCV RNA in serum have meanwhile established HCV clearance as the most precise endpoint to assess efficacy of antiviral therapy for HCV infection. ALT normalisation, on the other hand, is far less specific. However, due to its simple and inexpensive determination, ALT measurement is part of all routine biochemistry assessments. For this reason and for historical reasons, ALT normalisation maintains its role at least as a secondary efficacy endpoint. Liver histology, the third classical endpoint, represents the surrogate endpoint considered nearest to the 'true' endpoints of liver-related morbidity and mortality. All three of these measures were assessed in this study.

Impact of Treatment on HCV RNA Levels (Virological Response)

In the total population, baseline viral load varied widely. Under treatment, decreases in viral load were evident as early as Day 3 (the first on-treatment measurement), and minimum values were reached by Week 4. After Week 4, HCV RNA gradually increased, reaching levels near baseline in all treatment groups by Week 24 of observation. Baseline viral load was somewhat lower for cirrhotic patients than for non-cirrhotics, and variation between treatment groups at baseline was more pronounced among cirrhotics than among non-cirrhotics; this finding is most likely due to the small number of cirrhotic patients. Changes from baseline among cirrhotic patients followed the same general pattern seen in the total population: prompt decreases reaching a maximum between Weeks 4 and 12 and returning gradually to baseline thereafter. Viral load at baseline was significantly lower for Asians than for non-Asians. As seen in the other populations, viral load decreased promptly in the Asian population, reaching a maximum between Weeks 4 and 12 and returning to baseline by Week 24 of observation. There was no clear relation between response and dose in any population.

Patients with complete clearance of HCV RNA from the serum at the end of treatment at Week 48 were defined as complete HCV RNA responders. Twenty-two (22) patients showed complete HCV RNA response at Week 48 (8.3% of the total population). Complete response rates were similar in the cirrhotic and non-cirrhotic populations. In the Asian population, however, complete response rates were markedly higher than those in the total population. Asians accounted for 6 of the 22 complete responses at Week 48, representing a complete response rate of 26.1% compared to 6.6% for non-Asians: this difference was statistically significant. Response appeared to be dose-related in the total population, but a dose relation could not be established in the Asian population, possibly due to the small numbers of patients. The highest response rate among Asians occurred in the lowest dose group (44 mcg TIW; 2 of 6 or 33.3%).

In the total population, 56 patients (21.1%) showed HCV RNA clearance at least once during the study. Proportions of patients showing HCV RNA clearance at least once were similar between the cirrhotic and non-cirrhotic populations. However, 13 of 24 Asian patients showed clearance of HCV RNA at least once (56.5%, compared to 17.7% for non-Asians). The proportion of patients with at least one clearance increased with dose and frequency of administration in all populations but the cirrhotic subgroup, in which no pattern was clear.

The primary endpoint of the study was the rate of sustained virological response, defined as the absence of detectable HCV RNA in the serum at both the end of treatment (Week 48) and the end of 24 weeks of observation. Rates of sustained virological response were low: only 9 sustained responses were noted, representing a response rate of 3.4% in the total population. In the cirrhotic subgroup, only one sustained response was noted. Again, the Asian subgroup showed sustained response rates well above those in the total population. Five (5) of the 9 sustained responses occurred in Asian patients, leading to a response rate among Asians of 21.7% compared to only 1.6% for non-Asians (p<0.001). Among Asians, response rates by treatment group ranged from 16.7% to 28.8% and appeared to be dose-and frequency-related, although numbers of patients concerned were very small. The apparent dose-response relationship seen in the Asian population was also seen in the total population, in which response rates by treatment group ranged from 1.5% to 6.3%.

Among patients who achieved sustained virological response, viral load at baseline was lower than in the population as a whole. As observed for the full population, decreases were seen early (Day 3), generally reaching greatest magnitude (in the case of sustained responders, complete HCV RNA clearance) after 2 to 12 weeks of treatment. Four (4) out of 5 Asian sustained responders had undetectable viral loads by Week 2 (the earliest clearance was noted at Week 1); the remaining Asian patient achieved clearance by Week 4. In non-Asian sustained responders, decreases in HCV RNA occurred early (Day 3) but complete clearance was not achieved until Week 11 (one patient) or Week 48 (3 patients).

Impact of Treatment on ALT Levels (Biochemical Response)

Baseline ALT levels were significantly higher for Asians than for non-Asians: at Day 1 mean (±std) and median for Asians were 200.6 (±145.4) and 150 IU/l, compared to 137.3 (±88.4) and 106.5 IU/l for non-Asians (p=0.023).

In the total population 46 patients showed ALT normalisation at the end of treatment at Week 48 (17.3%). The percentage of patients with ALT nornalisation at Week 48 was slightly lower for cirrhotic patients (11.6%) compared to non-cirrhotic patients (18.4%). Again, Asians fared notably better than non-Asians (26.1% compared to 16.5%). There was no clear relation between ALT response at Week 48 and dose or frequency of administration.

A total of 37 patients showed ALT normalisation at the end of observation (Week 24): 13.9% of the total population; down from 17.3% at the end of treatment. The highest percentage of patients with normal ALT was seen in the 88 mcg QD group (20.6%); percentages in other treatment groups ranged from 10.8% to 13.4%. Only 2 cirrhotic patients (4.7%) had normal ALT at the end of observation compared to 15.7% of non-cirrhotics. Among non-Asians, only 9.9% had normal ALT at Week 24 of observation compared to 16.5% at the end of treatment; however, among Asians the normalisation rate had actually increased from 26.1% to 56.5%. Response appeared to be better with higher dose in the Asian population, but the numbers of patients concerned were very small.

Sustained ALT normalisation was defined as ALT within the normal range at both Week 48 of treatment and Week 24 of observation without abnormal results between these two measurements. Sustained normalisation was noted in only 14 patients in the total population (5.3%). Only one cirrhotic patient (assigned to 44 mcg QD) achieved sustained ALT normalisation (2.3%, compared to 5.8% for non-cirrhotics). Four (4) Asian patients showed sustained ALT normalisation (17.4%, compared to 4.1% for non-Asians): 2 were receiving 44 mcg QD and the others were receiving 88 mcg TIW. There was no apparent dose effect, but the numbers of patients concerned were very small.

The study also assessed elimination of HCV RNA and normalisation of ALT as a joint endpoint. Only 10 patients showed both HCV RNA clearance and ALT normalisation at the end of treatment at Week 48 (3.8% of the total population): these patients were distributed evenly across the 88 mcg TIW, 44 mcg QD and 88 mcg QD groups. No combined patients achieved both endpoints. Two (2) combined responders were Asian, for combined response rates of 8.7% for Asians and 3.3% for non-Asians. Only 8 patients achieved sustained clearance of HCV RNA combined with normal ALT at Week 24 of observation (3.0% of the total population). Two (2) of these patients were receiving 88 mcg TIW, 2 were receiving 44 mcg QD and 4 were receiving 88 mcg QD. None of the combined responders was cirrhotic. Notably, 4 of the combined responders were Asian, leading to combined response rates of 17.4% for Asians and 1.6% for non-Asians.

Impact of Treatment on Liver Histology (Histological Response)

Liver biopsies were obtained before and after the 48 weeks of treatment. As the evaluation method is based on comparison of pre- and post-treatment biopsies, only patients for whom both specimens were available and evaluable could be assessed for changes (176 patients in the total population). As for most variables assessed, changes in liver histology were generally similar between cirrhotic and non-cirrhotic patients. In contrast to other endpoints, changes in liver histology did not differ appreciably between the Asian and non-Asian populations: however, the numbers of patients with both pre- and post-treatment results were small, particularly among Asians (10 Asians and 166 non-Asians).

The total HAI grading score, obtained by summing up the grading components, is recognised as methodologically incorrect (Sheuer P J, 1996) but was calculated for comparison with other published studies. Baseline HAI scores ranged from 5.9 to 6.4, indicating moderate disease, and were generally comparable between treatment groups. For those patients with both pre- and post-treatment biopsies, HAI scores decreased from baseline in all treatment groups, with the greatest decreases occurring in the 44 mcg QD and 88 mcg QD groups and an overall decrease of −0.8. An overall decrease of −1.1 was observed in cirrhotic patients; dose relation was not evident, possibly due to small patient numbers. In Asian patients, HAI scores decreased in the two TIW dosing groups but increased in QD dosing groups for an overall change of −0.2. Caution is urged in interpretation of these results due to the extremely low numbers of patients with available biopsies.

Activity in the periportal and periseptal areas may be predictive of the subsequent development of cirrhosis. In the total population, piecemeal necrosis improved by one point in 27.3% of patients and by $\geq 2$ points in 16.5% overall; 33.5% of patients showed no change. Percentages of patients in the cirrhotic and Asian populations showing improvement and no change were similar to those in the total population with no evidence of a dose relationship in this parameter, but numbers of patients were small. No biopsy specimens showed signs of confluent necrosis, which is a rare histopathological finding in hepatitis C observed mainly in the most severe cases. Of the HAI components evaluated, focal lytic necrosis, apoptosis and focal inflammation showed the least improvement: 25.0% of the total population improved by one point, only 5.7% improved by $\geq 2$ points and 50.6% showed no change.

Percentages of cirrhotic and non-irrhotic patients showing improvement were similar, but the percentage with improvement by $\geq 2$ points was smaller among cirrhotics. Only 2 Asian patients showed improvement.

Portal inflammation improved by one point in 33.0% of the total population, with 11.9% improving by $\geq 2$ points and 30.7% showing no change. Cirrhotic patients were slightly less likely to show improvement by $\geq 2$ points and both cirrhotic and Asian patients were more likely to show no change; however, the numbers of patients in these populations were small. Overall, 32.2% of patients showed improvement by at least one point in liver architecture (fibrosis and cirrhosis), but only 7.9% improved by ≧2 points. Slightly over one third of patients (34.5%) showed no change from baseline to the end of treatment.

Exploratory Analyses

The most striking and surprising finding of this study by far was the difference in efficacy results between the Asian and non-Asian patient populations. There are no reports in the literature of such nature. Therefore, inferential analyses (Fisher's exact test and logistic regression) were employed in an exploratory manner to generate hypotheses, notably in relation to differences between Asian and non-Asian patients. It should be noted that there was a very large imbalance between the numbers of Asian and non-Asian patients. Therefore, caution is required in the interpretation of results of inferential analyses.

Fisher's exact test showed that Asians were significantly more likely than non-Asians to achieve complete HCV RNA clearance at Week 48 of treatment (unadjusted OR 5.0; CI for odds ratio [1.7-14.5]: p=0.006), at Week 24 of observation (unadjusted OR 8.2; CI for odds ratio [2.4-27.5); p=0.003) and at both time points (sustained virological response, the primary efficacy endpoint of the study: unadjusted OR 16.6; CI for odds ratio [4.1-67.31; p<0.001). Asians were also more likely than non-Asians to have normal serum ALT: the difference was not statistically significant at Week 48 of treatment (unadjusted OR 1.8; CI for odds ratio [0.7-4.8]; p=0.251), but at Week 24 of observation the unadjusted odds ratio for Asians vs. non-Asians was 11.9 (CI for odds ratio [4.7-29.9]; p<0.001), and the unadjusted odds ratio for Asians vs. non-Asians for sustained ALT normalisation was 4.9 (CI for odds ratio [1.4-17.1]; p=0.024).

Logistic regression analysis showed that age, sex, cirrhotic status, dose frequency and dose intensity were not significant predictors of sustained HCV RNA clearance. Both baseline HCV RNA and race were found to be significant, and the main model chosen included baseline HCV and race. Patients with low baseline HCV RNA were more likely to achieve a sustained virological response than patients with high baseline values (adjusted OR 1.07; CI for OR [0.95-1.20]), and Asians remained more likely to experience sustained virological response than non-Asians after adjustment for baseline HCV (adjusted OR 12.36; CI for OR [2.93-52.14]). Age, sex, cirrhotic status, baseline HCV RNA, dose regimen and dose intensity were not significant predictors of HCV RNA clearance at end of treatment at Week 48. However, race was highly significant (p=0.0065). Asians were more likely to achieve HCV RNA clearance at the end of treatment than non-Asians (unadjusted OR 5.0; CI for OR [1.7-14.5]). Race was the only significant explanatory variable for sustained ALT normalisation (p=0.0247): Asians were more likely to experience sustained ALT normalisation than non-Asians (unadjusted OR 4.9; CI for OR [1.4-17.1]).

Extent of exposure in terms of dose (both total dose and dose per kilogram) was also found to be a significant predictor of efficacy. However, it should be noted that extent of exposure is affected by treatment compliance, efficacy and tolerability, and that these results are therefore subject to bias and should be interpreted with caution.

Effect of Dose and Frequency of Administration

The impact of dose and frequency of administration was most apparent for HCV RNA clearance: HCV RNA clearance both at the end of treatment and at the end of observation appeared to be dose-related, with increasing rates from 44 mcg TIW to 88 mcg QD. However, the apparent dose-related trends were not statistically significant (see results of logistic regression analyses). There was no clear relation between ALT normalisation and dose or frequency of administration. In particular, sustained ALT normalisation did not show a dose effect; however, the numbers of patients concerned were small. No dose effect was noted for the joint endpoint of elimination of HCV RNA and normalisation of ALT, or for changes in liver histology.

DISCUSSION AND OVERALL CONCLUSIONS

The purpose of this study was to select the best dose and regimen of subcutaneous interferon-beta-1a for use in the treatment of patients with chronic hepatitis C resistant to interferon-alpha. At the time of study design, it was believed that doses higher than those obtainable with IFN-alpha would be necessary if non-response was due to emergence of resistant HCV genotypes, or if higher doses were required for any other reason to bring about an antiviral or immunomodulatory effect. Because IFN-beta is better tolerated than IFN-alpha, it was believed that higher SC doses of IFN-beta-1a could be administered with relatively little toxicity.

Doses for investigation in this study were chosen based on results of previous trials with natural and recombinant IFN-beta in CHC, which studied doses from 3 MIU (11 mcg) to 18 MIU (66 mcg) given three times a week for 3 to 6 months. A clear dose-response effect was demonstrated in these studies. However, response was not sustained suggesting that a higher dose and/or longer therapy would be required for sustained response. Therefore, 44 mcg TIW was chosen as a minimal effective dose for investigation. Viral kinetic studies have demonstrated a rapid turnover half-life for HCV, suggesting that daily rather than three times weekly dosing may be necessary to optimally suppress viral replication. Daily administration was therefore assessed in addition to the conventional schedule of three times a week. A phase I study carried out by the Applicant in patients with advanced cancer had shown that daily administration of doses of up to 18 $MIU/m^2$ IFN-beta-1a was well tolerated; however, dose-limiting toxicities occurred with 24 $MIU/m^2$. Therefore, it was decided to investigate daily administration of 24 MIU (88 mcg) in this study, as this dose was expected to be tolerated by most patients. The effectiveness and necessity of chronic SC dosing are supported by previous studies with other interferons. In 1997, a National Institutes of Health consensus panel recommended use of a 12-month regimen of IFN-alpha rather than 6 months (Editorial, 1997). It was therefore considered reasonable to examine response to 12 months of IFN-beta-1a.

In studies of antiviral therapy for CHC, the three classical outcomes employed are ALT normalisation, HCV-RNA clearance and improvement in liver histology. All three outcomes were assessed in this study.

However, the most striking and surprising finding of this study was the difference in efficacy results between the Asian and non-Asian patient populations. There are no such reports in the literature.

Under treatment, decreases in viral load were evident as early as Day 3 (the first on-treatment measurement), and minimum values were reached by Week 4. In the total population, 21.1% of patients had undetectable serum HCV RNA at least once during the study. Among cirrhotic patients, 18.6% showed HCV RNA clearance at least once compared to 21.5% for non-drrhotics. The Asian subgroup was distinguished by a much higher proportion of patients responding to treatment: 56.5% had undetectable serum HCV RNA at least once. At the end of treatment at Week 48, a total of 22 patients showed complete HCV RNA clearance (8.3% of the total population).

Complete response rates were similar in the cirrhotic and non-cirrhotic populations (7.0% and 8.5% respectively). In the Asian subgroup, however, complete response rates were markedly higher than those in the total population. Asians accounted for 6 of the 22 complete responses at Week 48, representing a complete response rate of 26.1% compared to 6.6% for non-Asians. The primary endpoint of the study was the rate of sustained virological response. In the overall study population, rates of sustained virological response were low: a total of 9 sustained responses were noted, representing a response rate of 3.4% for the total population. In the cirrhotic subgroup, only one sustained response was noted (a response rate of 2.3%), in an Asian patient receiving 44 mcg TIW. Again, the Asian subgroup showed sustained response rates well above those in the total population. Five (5) of the 9 sustained responses occurred in Asian patients leading to a response rate among Asians of 21.7% compared to only 1.6% for non-Asians. Among Asians, response rates by treatment group ranged from 16.7% to 28.6% and appeared to be dose- and frequency-related, although numbers of patients concerned were small. The apparent dose-response relationship seen in the Asian subgroup was also seen in the total population, in which response rates by treatment group ranged from 1.5% to 6.3%; however, these trends were not statistically significant. For non-Asian patients who achieved sustained virological response, some achieved sustained response after 11 weeks of treatment while others required up to the full 48 weeks of treatment. Asian patients showed HCV RNA clearance earlier than non-Asian patients, achieving HCV clearance as early as one week after start of treatment (range 1 to 4 weeks of treatment).

ALT levels were analysed as secondary endpoints. Following the end of treatment at Week 48, 46 patients in the total population showed ALT normalisation (17.3%). Rates of ALT nornalisation at Week 48 were slightly lower for cirrhotic patients compared to non-cirrhotic patients (11.6% compared to 18.4%), and Asians again fared notably better than non-Asians (26.1% compared to 16.5%). There was no clear relation between ALT response and dose or frequency of administration. In the total population, 37 patients showed normal serum ALT at the end of the observation period (13.9%: down from 17.3% at the end of treatment). Among cirrhotic patients, only 4.7% showed normal ALT at the end of observation. Among non-Asians, only 9.9% showed normal ALT at Week 24 of observation compared to 16.5% at the end of treatment; however, the nornalisation rate among Asians had actually increased, from 26.1% to 56.5%. Sustained ALT normalisation was noted in only 14 patients in the total population (5.3%). Only one cirrhotic patient achieved sustained normalisation of ALT (2.3%, compared to 5.8% for noncirrhotics). Four (4) of the 14 patients showing sustained ALT normalisation were Asian, leading to a normalisation rate of 17.4% for Asians compared to 4.1% for non-Asians. In the total population, only 10 patients showed both HCV RNA clearance and ALT normalisation at the end of treatment at Week 48 (3.8%). No cirrhotic patients achieved both endpoints. Two (2) of the combined responders were Asian, for combined response rates of 8.7% for Asians and 3.3% for non-Asians. Sustained clearance of HCV RNA combined with a normalised ALT at Week 24 of observation was achieved only by 8 patients in the total population (3.0%). None of the combined responders was cirrhotic. Notably, 4 of the combined responders were Asian, leading to combined response rates of 17.4% for Asians and 1.6% for non-Asians.

As for most parameters assessed, changes in liver histology did not differ substantially between the cirrhotic and non-cirrhotic populations. However, in contrast to other endpoints, changes in liver histology did not differ appreciably between the Asian and non-Asian populations. This may be related to the small numbers of Asian patients with post-treatment results (10 Asians compared to 166 non-Asians).

Inferential analyses (Fisher's exact test and logistic regression) were employed in an exploratory manner to generate hypotheses, notably in relation to differences between Asian and non-Asian patients. Asians were found to be significantly more likely than non-Asians to achieve complete HCV RNA clearance at Week 48 of treatment, at Week 24 of observation and at both time points. Asians were also more likely than non-Asians to have normal serum ALT.

The impact of dose and frequency of administration was most apparent for HCV RNA clearance; however, the observed dose-related trends were not statistically significant. The impact of dose and frequency of administration on ALT levels was more obscure.

The low discontinuation rate for the TIW regimen versus much higher rates for the QD groups clearly indicated that patient compliance and tolerability limits were being reached. Because of the increased dropout rates in the QD dose groups, it should be emphasised that any conclusions drawn for these groups apply to small, selected (and possibly biased) patient populations. However, with this caveat in mind, it should also be noted that despite the high doses and intense frequency employed In this study, most of the commonly reported events fell into the categories of constitutional symptoms known to be associated with interferons and application site disorders, and most were mild to moderate in severity.

REFERENCE LIST

Alter M J et al., *N. Engl. J. Med.*, 327, 1899-1905, 1992;
Alter M J et al., *N. Engl. J. Med.*, 341, 556-562, 1999;
Armitage P et al., Statistical Methods in Medical Research, $2^{nd}$ ed . London: Macmillan, 1990
Bacon B R et al., *Hepatology*, 22, 152A-152A, 1995;
Bedossa P et al., *Hepatology* 24(2):289-293, 1996;
Bonkovsky H L. et al., *Hepatology*, 25(3), 759-768, 1997;
Brand C M et al., *J. Interferon Res.*, 13, 121-125, 1993;
Cavalli-Sforza L, *Scientific American*, 72-78, November 1991
Conjeevaram H S et al., *Hepatology*, 22(4 Pt 1), 1326-1329. 1995;
Cuzick J., *Statistics in Medicine*, 4, 87-90, 1985;
Davis G L, *J. Hepatol.*, 11, S72-S77, 1990;
Derynk R. et al., *Nature* 285, 542-547, 1980;
Douglas D D. et al., *Dig Dis Sci.* 38, 601-607, 1993;
Editorial. *Scrip*, 2221, 25-25, 1997;
Habersetzer et al., *Liver,* 20 437-441: 2000;
Habersetzer et al., *Liver,* 20, 438, 4th line, 2000;
Hoofnagle J H, *N. Engl. J. Med.*, 336 (5):347-356, 1997;
Ishak K, *J. Hepatol.* 22, 696-699, 1995;
Kishiara et al., *Fukukoka Acta Med.*, 86(4), 113-20, 1995;
Lindsay K L, *Hepatology*, 24, 1034-1040, 1996;
Lok A S F et al., *Hepatology*, 1266-1270, 1990;
Mark D. F. et al., *Proc. Natl. Aced. Sci. U.S.A.*, 81 (18) 5662-5666, 1984;

McCaughan G W, *J. Gastroenterol. Hepatol.*, 15, G90-G93, 2000;
McHutchison J G et al., *N. Engl. J. Med.*, 339(21),1485-1492, 1998;
McIntyre N. et al., In: Weatherall D J, et al., editors. Oxford Textbook of Medicine.
Oxford University Press, 2085-2100, 1996:
McOmish F et al., *J. Clin. Microbiol.*, 32(4):884-892, 2000;
Milella M M et al., *Liver*, 13:146-150, 1993;
O'Brien P C et al., *Biometrics*, 40, 1079-1087, 1984;
Omata M et al., *Lancet*, 338, 914-915, 1991;
Perez R. et al., *J. Virol. Hepat.*, 2(2), 103-6), 1995;
Piccinino F., *Arch. Virol. Suppl.*, 8, 257-263, 1993;
Poynard T, et al., *Lancet*, 352, 1426-1432, 1998;
Poynard T. et al., *Hepatology*, 24, 778-789, 1996;
PRISMS Study Group, *Neurology*, 56(12):1628-1636, 2001.
Saracco G et al., *Hepatology*, 18, 1300-1305, 1993;
Scheuer P J et al., *J. Gastroenterol. Hepatol.*, 8, 1141-1143, 1996;
Schvarcz R., *Scand. J. Infect Dis.*, 21, 617-625, 1989;
Shepard H. M. et al., *Nature*, 294, 563-565, 1981;
Tabor E et al, *J. Natl. Cancer Inst.*, 84 (2), 86-90, 1992;
Takeda T., *Gastroenterol. Jpn.*, 28, 104-108, 1993;
Tundo L. *Hepatology*, 260A-260A,
Wilkinson T, *Curr. Op. Invst. Drug*, 2(11), 1516-22, 2002
Zein N N et al., *Ann. Intern. Med.*, 125, 634-639, 1996.

The invention claimed is:

1. A method of treating hepatitis C virus infections comprising the subcutaneous administration of an effective amount of a composition comprising interferon-beta (IFN-β) to Asian patients that had failed to respond to a previous treatment with interferon-α.

2. The method according to claim 1, wherein said patients which failed to respond to a previous treatment with interferon-α have undergone at least 12 weeks of treatment with IFN-α at a dose of at least 3 Million International Units (MIU) 3 times a week, with one of the following outcomes: (a) failure to normalise serum alanine aminotransferase (ALT), or (b) normalisation of ALT followed by breakthrough (ALT elevation) before the end of therapy and said IFN-β is administered according to a schedule selected from the group consisting of: 12 MIU (44 mcg) IFN-β-1a three times a week, 12 MIU (44 mcg) IFN-β-1a daily, 24 MIU (88 mcg) IFN-β-1a three times a week, and 24 MIU (88 mcg) IFN-β-1a daily.

3. The method according to claim 1, wherein said IFN-β is administered according to a schedule selected from the group consisting of: 12 MIU (44 mcg) IFN-β-1a three times a week, 12 MIU (44 mcg) IFN-β-1a daily, 24 MIU (88 mcg) IFN-β-1a three times a week, and 24 MIU (88 mcg) IFN-β-1a daily.

4. The method according to claim 1, wherein said composition comprises IFN-β and an additional anti-viral agent.

5. The method according to claim 4, wherein said IFN-β is administered according to a schedule selected from the group consisting of: 12 MIU (44 mcg) IFN-β-1a three times a week, 12 MIU (44 mcg) IFN-β-1a daily, 24 MIU (88 mcg) IFN-β-1a three times a week, and 24 MIU (88 mcg) IFN-β-1a daily.

6. The method according to claim 1, wherein the IFN-β is recombinant IFN-β-1a.

7. The method according to claim 6, wherein said recombinant IFN-β-1a is administered according to a schedule selected from the group consisting of: 12 MIU (44 mcg) recombinant IFN-β-1a three times a week, 12 MIU (44 mcg) recombinant IFN-β-1a daily, 24 MIU (88 mcg) recombinant IFN-β-1a three times a week, and 24 MIU (88 mcg) recombinant IFN-β-1a daily.

* * * * *

UNITED STATES PATENT AND TRADEMARK OFFICE
CERTIFICATE OF CORRECTION

PATENT NO. : 7,344,709 B2
APPLICATION NO. : 10/515032
DATED : March 18, 2008
INVENTOR(S) : Ian Parsons, Theodor Wee Tit Gin and Birgit J. Maschek It is certified that error appears in the above-identified patent and that said Letters Patent is hereby corrected as shown below:

Column 7,
Line 7, "an amino add" should read --an amino acid--.
Line 8, "native amino add" should read --native amino acid--.
Line 43, "of formami de in" should read --of formamide in--.

Column 8,
Line 40, "HCV patents" should read --HCV patients--.
Line 61, "treatment In" should read --treatment. In--.

Column 10,
Line 12, "PO  Peros—By mouth" should read --PO  Per os—By mouth--.
Line 60, "[1.7-14.51]" should read --[1.7-14.5]--.

Column 11,
Line 50, "(Bedossa P et al., 1998)" should read --(Bedossa P et al., 1996)--.

Column 12,
Line 49, "ascites. hepatic" should read --ascites, hepatic--.

Column 21,
Line 9, "notably In relation" should read --notably in relation--.
Line 24, "confidence i ntervals" should read --confidence intervals--.

Column 23,
Line 4, "those In the" should read --those in the--.

Column 24,
Line 58, "only In specific" should read --only in specific--.

Column 29,
Line 30, "$8.7 \times 10^{\not=}$" should read --$8.7 \times 10^6$--.

Column 33,
Line 25, "nornalisation" should read --normalisation--.

UNITED STATES PATENT AND TRADEMARK OFFICE
CERTIFICATE OF CORRECTION

PATENT NO. : 7,344,709 B2
APPLICATION NO. : 10/515032
DATED : March 18, 2008
INVENTOR(S) : Ian Parsons, Theodor Wee Tit Gin and Birgit J. Maschek It is certified that error appears in the above-identified patent and that said Letters Patent is hereby corrected as shown below:

Column 34,
Line 57, "non-irrhotic" should read --non-cirrhotic--.

Column 35,
Line 24, "[4.1-67.31;" should read --[4.1-67.3];--.

Column 36,
Line 65, "non-drrhotics" should read --non-cirrhotics--.

Column 37,
Line 40, "nornalisation" should read --normalisation--.
Line 56, "noncirrhotics" should read --non-cirrhotics--.

Column 38,
Line 33, "employed In this" should read --employed in this--.
Line 66, "Proc. Natl. Aced." should read --Proc. Natl. Acad.--.

Signed and Sealed this

Twenty-sixth Day of August, 2008

JON W. DUDAS
*Director of the United States Patent and Trademark Office*